US009668946B2

(12) United States Patent
Moszner et al.

(10) Patent No.: US 9,668,946 B2
(45) Date of Patent: Jun. 6, 2017

(54) DENTAL MATERIALS BASED ON MONOMERS HAVING DEBONDING-ON-DEMAND PROPERTIES

(75) Inventors: Norbert Moszner, Mauren (LI); Iris Lamparth, Grabs (CH); Thorsten Bock, Tosters (AT); Urs Karl Fischer, Arbon (CH); Ulrich Salz, Lindau (DE); Volker Rheinberger, Vaduz (LI); Robert Liska, Schleinbach (AT)

(73) Assignee: Ivoclar Vivadent AG, Schaan (LI)

( * ) Notice: Subject to any disclaimer, the term of this patent is extended or adjusted under 35 U.S.C. 154(b) by 231 days.

(21) Appl. No.: 14/343,297

(22) PCT Filed: Sep. 10, 2012

(86) PCT No.: PCT/EP2012/067679
§ 371 (c)(1),
(2), (4) Date: Jul. 21, 2014

(87) PCT Pub. No.: WO2013/034777
PCT Pub. Date: Mar. 14, 2013

(65) Prior Publication Data
US 2014/0329929 A1    Nov. 6, 2014

(30) Foreign Application Priority Data

Sep. 8, 2011 (EP) .................................... 11180645

(51) Int. Cl.
*A61K 6/083* (2006.01)
*A61K 6/00* (2006.01)
(Continued)

(52) U.S. Cl.
CPC .......... *A61K 6/0835* (2013.01); *A61K 6/0002* (2013.01); *A61K 6/0023* (2013.01);
(Continued)

(58) Field of Classification Search
CPC .................................................... A61K 6/083
See application file for complete search history.

(56) References Cited

U.S. PATENT DOCUMENTS

| 6,764,569 B1 | 7/2004 | Becher et al. |
| 7,935,131 B2 | 5/2011 | Anthamatten et al. |

(Continued)

FOREIGN PATENT DOCUMENTS

| DE | 19832629 A1 | 2/2000 |
| JP | 2005232412 A | * 9/2005 |

(Continued)

OTHER PUBLICATIONS

English machine translation of Kasai et al. (JP 2005-232412); generated Jan. 12, 2016.*

Braun, D., et al., Synthese and Zerfall von Azionitiatoren, I., Monatshefte für Chemie, 1982, vol. 113, pp. 1403-1414.
McKillip, W.J., et al., Furan and Derivatives, Ullmann's Encyclopedia of Industrial Chemistry, 5th Ed., vol. A 12, Formamides to Hexamthylenediamine, VCH, Weinheim etc., 1989, pp. 119-134.
Folmer, B.J.B., et al., Supramolecular Polymer Materials: Chain Extension of Telechelic Polymers Using a Reactive Hydrogen-Bonding Synthon, Adv. Mater., 2000, vol. 12, No. 12, pp. 874-878.
Becker, H.G.O., et al., Chapter 4.4.4 [4+2]-Cycloadditionene (Diels-Alder-Reaktion), Organikum, Organisch-chemisches Grundpraktikum, Wiley-VCH, 2001, vol. 21, Weinheim pp. 330-333.
Quinn, S., Chemical blowing agents: providing production, economic and physical improvements to a wide range of polymers, Plastics, Additives & Compounding, May 2001, vol. 3, pp. 16-21.
Walter, W., et al., Chapter 7.1.3.3 Paal-Knorr-Synthese, Beyer-Walter, Lehrbuch der Organischen Chemie, S. Hirzel Verlag, Stuttgart and Liepsiz, 2004, vol. 24, p. 769.
Rowan, S.J., et al., Metal-ligand induced supramolecular polymerization: A route to responsive materials, Faraday Discussions, 219 Aug. 2004, vol. 128, pp. 43-53.
Sivakova, S., et al., Nucleobases as supramolecular motifs, Chem. Soc. Rev., Dec. 6, 2004, vol. 34, pp. 9-21.
De Greef, T.F.A., et al., Supramolecular polymers, Nature, May 8, 2008, vol. 453, pp. 171-173.
Fox, J.D., et al., Supramolecular Polymerizations and Main-Chain Supramolecular Polyers, Macromolecules, 2009, vol. 42, pp. 6823-6835.
Burattini, S., et al., A Healable Supremolecular Polymer Blend Based on Aromatic π-πStacking and Hydrogen-Bonding Interactions, J. Am. Chem. Soc., 2010, vol. 132, pp. 12051-12058.

(Continued)

*Primary Examiner* — Michael Pepitone
(74) *Attorney, Agent, or Firm* — Ann M. Knab; Thad McMurray

(57) ABSTRACT

The invention relates to a dental restorative material which comprises a thermolabile or photolabile polymerizable compound of Formula I:

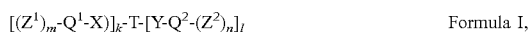

in which T represents a thermolabile or photolabile group, $Z^1$ and $Z^2$ in each case independently represent a polymerizable group selected from vinyl groups, $CH_2$=$CR^1$—CO—O— and $CH_2$=$CR^1$—CO—$NR^2$— or an adhesive group selected from —Si(OR)$_3$, —COOH, —O—PO(OH)$_2$, —PO(OH)$_2$, —SO$_2$OH and —SH, wherein at least one $Z^1$ or $Z^2$ is a polymerizable group, $Q^1$ in each case independently is missing or represents an (m+1)-valent linear or branched aliphatic $C_1$-$C_{20}$ radical which can be interrupted by —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—, $Q^2$ in each case independently is missing or represents an (n+1)-valent linear or branched aliphatic $C_1$-$C_{20}$ radical which can be interrupted by —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—, X and Y in each case independently are missing or represent —O—, —S—, CO—O—, —O—CO—, —CO—$NR^3$—, —$NR^3$—CO—, —O—CO—$NR^3$—, —$NR^3$—CO—O— or —$NR^3$—CO—$NR^3$—, R, $R^1$, $R^2$ and $R^3$ in each case independently represent H or a $C_1$-$C_7$ alkyl radical and k, l, m and n in each case independently are 1, 2 or 3.

16 Claims, No Drawings

(51) Int. Cl.
*C07D 239/47* (2006.01)
*C07F 3/06* (2006.01)
*C08F 122/22* (2006.01)

(52) U.S. Cl.
CPC ............ *A61K 6/083* (2013.01); *C07D 239/47* (2013.01); *C07F 3/06* (2013.01); *C08F 122/22* (2013.01)

(56) References Cited

U.S. PATENT DOCUMENTS

| | | | |
|---|---|---|---|
| 8,247,524 B2 | 8/2012 | Janssen et al. | |
| 8,552,086 B2 | 10/2013 | Karim et al. | |
| 2005/0182148 A1 | 8/2005 | Gaud et al. | |
| 2006/0165753 A1 | 7/2006 | Richard | |
| 2007/0027229 A1* | 2/2007 | Moszner | A61K 6/0023 523/109 |
| 2007/0142494 A1 | 6/2007 | Kalgutkar et al. | |
| 2007/0142497 A1 | 6/2007 | Kalgutkar et al. | |
| 2007/0142498 A1 | 6/2007 | Brennan et al. | |
| 2008/0076848 A1* | 3/2008 | Jin | A61K 6/083 522/162 |
| 2008/0277814 A1* | 11/2008 | Moszner | A61K 6/083 264/19 |
| 2010/0021839 A1* | 1/2010 | Farrugia | G03G 9/0804 430/108.4 |
| 2012/0114952 A1 | 5/2012 | Bauer et al. | |

FOREIGN PATENT DOCUMENTS

| | | |
|---|---|---|
| WO | 02/46260 A1 | 6/2002 |
| WO | 2008/005173 A1 | 1/2008 |
| WO | 2010/002262 A1 | 1/2010 |
| WO | 2010/128042 A1 | 11/2010 |

OTHER PUBLICATIONS

Burnworth, M., et al., Optically healable supramolecular polymers, Nature, Apr. 21, 2011, vol. 472, pp. 334-338.

Wojtecki, R.J., et al., Using the dynamic bond to access macroscopically responsive structurally dynamic polymers, Nature Materials, Dec. 15, 2010, vol. 10, pp. 14-27.

Aida, T., et al., Functional Supramolecular Polymers, Science, Feb. 17, 2012, vol. 335, pp. 813-817.

* cited by examiner

DENTAL MATERIALS BASED ON MONOMERS HAVING DEBONDING-ON-DEMAND PROPERTIES

CROSS-REFERENCE TO RELATED APPLICATIONS

This application is a National Stage application of International patent application PCT/EP2012/067679 filed on Sep. 10, 2012, which claims priority to European patent application No. 11180645.1 filed on Sep. 8, 2011, the disclosures of which are incorporated herein by reference in their entirety.

The present invention relates to monomers with debonding-on-demand (DoD) properties and their use as monomer components in dental materials, in particular for preparing adhesives and cements.

Adhesive bonds that can be debonded again are increasingly important in various technological fields. Examples are the detachment of components within the framework of automated manufacturing processes, the repair of complex components with adhesively bonded subcomponents or the simplification of the separation of materials when recycling such components at the end of the product's life. The debonding of adhesive bonds can be achieved on demand by significantly reducing the strength of the adhesive bond layer e.g. by heating.

Thus DE 198 32 629 A1 describes an adhesive system for forming reversible adhesive bonds based on polyurethanes, polyureas or epoxy resins, in which an additional component can be activated by introducing energy such that a degradation of the adhesive components takes place. For example, organic bases or acids which bring about a degradation of the adhesive resin can be released from blocked precursors by introducing heat or radiation energy.

WO 2010/128042 A1 describes industrial adhesive compositions for debondable adhesive bonds for aircraft or motor vehicle construction which consist of a customary adhesive matrix and a particulate expansion material such as e.g. azodicarbonamide. The components are debonded by heating the adhesive bond at least to the expansion temperature of the expansion material.

In dentistry, the debonding of adhesive bonds is important among other things in orthodontics, where brackets which are adhesively bonded to the tooth surface to correct malocclusions must be removed again without damaging the tooth enamel after successful correction. Moreover, in the case of repair or complete replacement of high-strength ceramic restorations or crowns which are laborious to remove mechanically, cement bonds that can be easily softened or separated would be advantageous.

In connection with orthodontic applications, US 2007/0142498 A1 describes dental compositions which contain thermally controllable additives such as e.g. thermoplastic polymers.

US 2007/0142497 A1 describes dental compositions based on dimethacrylates with acid-labile tertiary carbonate groups and photoacids such as e.g. triarylsulphonium salts. These compositions can be photochemically cured with suitable initiators such as for instance the bisacyl phosphine oxide Irgacure 819 with light in the visible range (photobonding) and softened again by irradiation with UV light at increased temperature (photothermal debonding).

It is an object of the invention to provide adhesive dental restorative materials which are polymerizable, display good substrate adhesion in particular to the tooth structure and/or dental ceramics and allow a debonding from the substrate by introducing heat, and are thus suitable above all for preparing adhesives or composite cements with debonding-on-demand properties.

This object is achieved according to the invention by dental restorative materials based on a thermolabile or photolabile polymerizable compound of Formula I:

in which

T represents a thermolabile or photolabile group, $Z^1$ and $Z^2$ in each case independently represent a polymerizable group selected from vinyl groups, $CH_2=CR^1-CO-O-$ and $CH_2=CR^1-CO-NR^2-$ or an adhesive group selected from $-Si(OR)_3$, $-COOH$, $-O-PO(OH)_2$, $-PO(OH)_2$, $-SO_2OH$ and $-SH$, wherein at least one $Z^1$ or $Z^2$ is a polymerizable group, $Q^1$ in each case independently is missing or represents an (m+1)-valent linear or branched aliphatic $C_1$-$C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, $Q^2$ in each case independently is missing or represents an (n+1)-valent linear or branched aliphatic $C_1$-$C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3$, X and Y in each case independently are missing or represent $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3$, R, $R^1$, $R^2$ and $R^3$ in each case independently represent H or a $C_1$-$C_7$ alkyl radical and k, l, m and n in each case independently are 1, 2 or 3.

In an embodiment, at least one $Z^1$ or $Z^2$ is a polymerizable group and at least one $Z^1$ or $Z^2$ is an adhesive group. In this context those compounds of Formula I in which one of $Z^1$ and $Z^2$ represents a polymerizable group and the other of $Z^1$ and $Z^2$ represents an adhesive group are preferred. In another embodiment, $Z^1$ and $Z^2$ both represent a polymerizable group.

The indication that a radical can be interrupted by a group, such as for example $-O-$, is to be understood such that the group is inserted into the carbon chain of the radical, i.e. is bordered on both sides by carbon atoms. The number of these groups is therefore at least 1 less than the number of carbon atoms and the groups cannot be terminal. According to the invention, radicals which are not interrupted by the named groups are preferred.

According to the invention, only those compounds which are compatible with the chemical valence theory are considered.

Those compounds of Formula I are particularly preferred in which in each case independently of each other one of $Z^1$ and $Z^2$ in each case independently represents a polymerizable group selected from $CH_2=CR^1-CO-O-$ and $CH_2=CR^1-CO-NR^2-$ and the other of $Z^1$ and $Z^2$ in each case independently represents a polymerizable group selected from $CH_2=CR^1-CO-O-$ and $CH_2=CR^1-CO-NR^2-$ or preferably an adhesive group selected from $-Si(OR)_3$, $-COOH$, $-O-PO(OH)_2$, $-PO(OH)_2$, $-SO_2OH$ and $-SH$, $Q^1$ in each case independently is missing or represents an (m+1)-valent linear or branched aliphatic $C_1$-$C_{10}$ radical which can be interrupted by $-O-$, $-CO-O-$, $-O-CO-$, $-CO-NR^3-$, or $-NR^3-CO-$, $Q^2$ in each case independently is missing or represents an (n+1)-valent linear or branched aliphatic $C_1$-$C_{10}$ radical which can be interrupted by —O—, —CO—O—, —O—CO—, —CO—NR$^3$— or —NR$^3$—CO—, X and Y in each case independently are missing or represent —O—, —CO—O—, —O—CO—, —CO—NR$^3$— or —NR$^3$—CO—, R in each case independently is H, $CH_3$ or $C_2H_5$, $R^1$ in each case independently is H or $CH_3$, $R^2$ in each case independently is H, $CH_3$ or $C_2H_5$, $R^3$ in each case independently is H, $CH_3$ or $C_2H_5$, and/or k, l, m and n in each case independently are 1 or 2.

Compounds in which all the variables each have one of the preferred meanings defined above are particularly preferred.

In a preferred embodiment, T is a thermolabile group. Those compounds of Formula I are preferred in this context in which $Z^1$ and $Z^2$ in each case independently represent a polymerizable group selected from vinyl groups, $CH_2$=$CR^1$—CO—O— and $CH_2$=$CR^1$—CO—NR$^2$— or an acid group selected from —O—PO(OH)$_2$, —PO(OH)$_2$ and —SO$_2$OH, wherein at least one $Z^1$ or $Z^2$ is a polymerizable group and at least one $Z^1$ or $Z^2$ is an acid group, $Q^1$ in each case independently is missing or represents an (m+1)-valent linear or branched aliphatic $C_1$-$C_{10}$ radical which can be interrupted by —O—, —S—, —CO—O—, —O—CO—, —CO—NR$^3$— or —NR$^3$—CO—, $Q^2$ in each case independently is missing or represents an (n+1)-valent linear or branched aliphatic $C_1$-$C_{10}$ radical which can be interrupted by —O—, —S—, —CO—O—, —O—CO—, —CO—NR$^3$— or —NR$^3$—CO—, X and Y in each case independently are missing or represent —O—, —S—, —CO—O—, —O—CO—, —CO—NR$^3$— or —NR$^3$—CO—, $R^1$, $R^2$ and $R^3$ in each case independently represent H or a $C_1$-$C_7$ alkyl radical and k, l, m and n in each case independently are 1, 2 or 3.

In this context those compounds of Formula I in which one of $Z^1$ and $Z^2$ represents a polymerizable group and the other of $Z^1$ and $Z^2$ represents an acid group are preferred.

Those compounds of Formula I are particularly preferred in this context in which in each case independently of each other one of $Z^1$ and $Z^2$ in each case independently represents a polymerizable group selected from $CH_2$=$CR^1$—CO—O— and $CH_2$=$CR^1$—CO—NR$^2$— and the other of $Z^1$ and $Z^2$ in each case independently represents an acid group selected from —O—PO(OH)$_2$ and —PO(OH)$_2$ and —SO$_2$OH, $Q^1$ in each case independently is missing or represents an (m+1)-valent linear or branched aliphatic $C_1$-$C_{10}$ radical which can be interrupted by —O—, —CO—O—, —O—CO—, —CO—NR$^3$— or —NR$^3$—CO—, $Q^2$ in each case independently is missing or represents an (n+1)-valent linear or branched aliphatic $C_1$-$C_{10}$ radical which can be interrupted by —O—, —CO—O—, —O—CO—, —CO—NR$^3$— or —NR$^3$—CO—, X and Y in each case independently are missing or represent —O—, —CO—O—, —O—CO—, —CO—NR$^3$— or —NR$^3$—CO—, $R^1$ in each case independently is H or $CH_3$, $R^2$ in each case independently is H, $CH_3$ or $C_2H_5$, $R^3$ in each case independently is H, $CH_3$ or $C_2H_5$, and/or k, l, m and n in each case independently are 1 or 2.

Compounds in which all the variables each have one of the preferred meanings defined above are particularly preferred.

Suitable thermolabile groups are known per se. These are characterized according to the invention in that they contain one or more thermolabile covalent bonds. Preferred thermolabile groups with thermolabile covalent bonds include thermolabile cycloaddition adducts such as Diels-Alder adducts, hetero-Diels-Alder adducts as well as thermolabile alkoxyamine, oxime-ester, oxime-urethane or azo groups. Examples of thermolabile groups are also described in R. J. Wojtecki et al., Nature Materials 2011, 10, 14-27.

In particular, those compounds of Formula I are preferred in which T is a thermolabile group which is selected from the group consisting of:

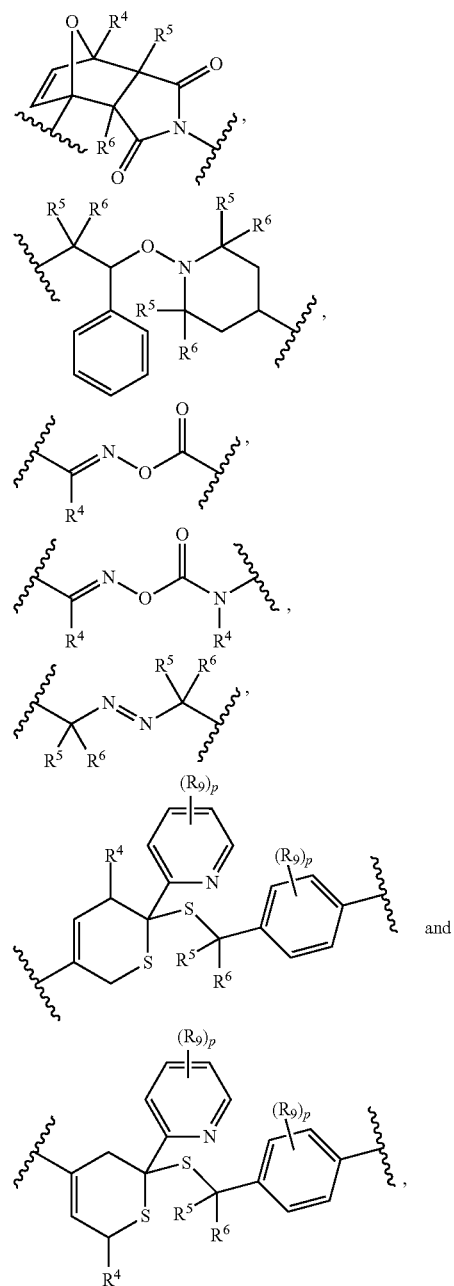

wherein:

$R^4$ is H or a $C_1$-$C_{10}$ alkyl radical, $R^5$ is H, a $C_1$-$C_5$ alkyl radical, F or CN, $R^6$ is H, a $C_1$-$C_5$ alkyl radical, F or CN,
$R^9$ in each case independently is $CH_3$, $C_2H_5$, $OCH_3$ or $OC_2H_5$ and
p in each case independently is 0, 1, 2 or 3.

According to the invention, dental materials in which the thermolabile polymerizable compound of Formula I is a Diels-Alder adduct of Formula II are particularly preferred:

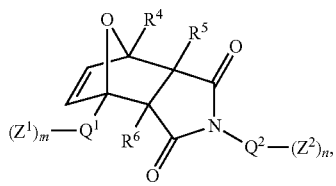

Formula II wherein the given variables have the meanings defined above. According to the invention, Formula II comprises both pure exo products or pure endo products and mixtures of exo and endo products.

In this context those compounds of Formula II are preferred in which in each case independently of each other
one of $Z^1$ and $Z^2$ in each case independently represents a polymerizable group selected from $CH_2$=$CR^1$—CO—O— and $CH_2$=$CR^1$—CO—$NR^2$— and the other of $Z^1$ and $Z^2$ in each case independently represents a polymerizable group selected from $CH_2$=$CR^1$—CO—O— and $CH_2$=$CR^1$—CO—$NR^2$— or preferably an adhesive group selected from —Si(OR)$_3$, —COOH, —O—PO(OH)$_2$, —PO(OH)$_2$, —SO$_2$OH and —SH,
$Q^1$ in each case independently is missing or represents an (m+1)-valent linear or branched aliphatic $C_1$-$C_{15}$ radical, preferably a $C_1$-$C_{10}$ radical, preferably a $C_1$-$C_8$ radical, in particular a $C_2$-$C_6$ radical and particularly preferably a $C_1$-$C_2$ radical, which can be interrupted by —O—, —CO—O—, —O—CO—, —CO—$NR^3$—, —$NR^3$—CO—, —O—CO—$NR^3$—, —$NR^3$—CO—O— or —$NR^3$—CO—$NR^3$—,
$Q^2$ in each case independently is missing or represents an (n+1)-valent linear or branched aliphatic $C_1$-$C_{15}$ radical, preferably a $C_1$-$C_{10}$ radical, preferably a $C_1$-$C_8$ radical, in particular a $C_2$-$C_6$ radical and particularly preferably a $C_2$-$C_3$ radical which can be interrupted by —O—, —CO—O—, —O—CO—, —CO—$NR^3$—, —$NR^3$—CO—, —O—CO—$NR^3$—, —$NR^3$—CO—O— or —$NR^3$—CO—$NR^3$—,
R in each case independently is $CH_3$ or $C_2H_5$,
$R^1$ in each case independently is H or $CH_3$,
$R^2$ in each case independently is H, $CH_3$ or $C_2H_5$,
$R^3$ in each case independently is H, $CH_3$ or $C_2H_5$,
$R^4$ is H, $CH_3$ or $C_2H_5$.
$R^5$ is H, F or CN and in particular H,
$R^6$ is H, F or CN and in particular H and/or
m and n in each case independently are 1 or 2.

Compounds of Formula II are quite particularly preferred in which in each case independently of each other
one of $Z^1$ and $Z^2$ in each case independently represents a polymerizable group selected from $CH_2$=$CR^1$—CO—O— and $CH_2$=$CR^1$—CO—$NR^2$— and the other of $Z^1$ and $Z^2$ in each case independently represents a polymerizable group selected from $CH_2$=$CR^1$—CO—O— and $CH_2$=$CR^1$—CO—$NR^2$— or preferably an adhesive group selected from —Si(OR)$_3$, —O—PO(OH)$_2$, —PO(OH)$_2$ and —SH, $Q^1$ represents a methylene or ethylene radical,
$Q^2$ represents an ethylene or propylene radical,
R in each case independently is $CH_3$ or $C_2H_5$,
$R^1$ in each case independently is H or $CH_3$,
$R^2$ in each case independently is H, $CH_3$ or $C_2H_5$,
$R^3$ in each case independently is H, $CH_3$ or $C_2H_5$,
$R^4$ is H, $CH_3$ or $C_2H_5$,
$R^5$ is H, F or CN and in particular H,
$R^6$ is H, F or CN and in particular H and/or
m and n in each case are 1.

Compounds in which all the variables each have one of the preferred meanings defined above are particularly preferred.

In another embodiment, T is a photolabile group. Suitable photolabile groups are known per se. These are usually characterized in that they contain one or more photolabile covalent bonds. Preferred photolabile groups with photolabile covalent bonds include benzoin ethers, oxyalkylphenylacetophenones, dialkyloxyacetophenones, benzoyldiphenylphosphine oxides, dibenzoylphenylphosphine oxides, dialkylbenzoyl and dialkyldibenzoyl germanium derivatives.

In particular, those compounds of Formula I are preferred in which T is a photolabile group which is selected from the group consisting of:

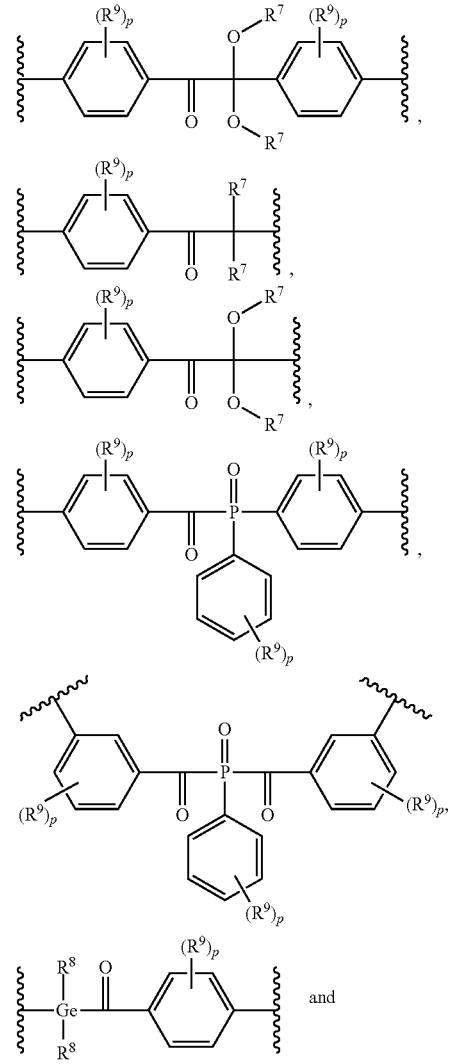

and

-continued

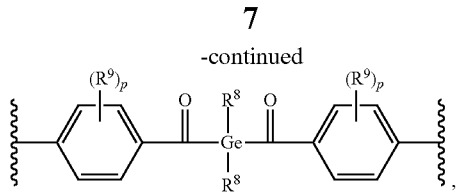

wherein:
$R^7$ in each case independently represents a $C_1$-$C_{10}$ alkyl radical,
$R^8$ in each case independently represents a $C_1$-$C_7$ alkyl radical,
$R^9$ in each case independently is $CH_3$, $C_2H_5$, $OCH_3$ or $OC_2H_5$ and
p in each case independently is 0, 1, 2 or 3.

According to the invention, dental materials in which the photolabile polymerizable compound of Formula I is a dibenzoylphenylphosphine oxide of Formula III or a dialkyldibenzoyl germanium derivative of Formula IV are particularly preferred:

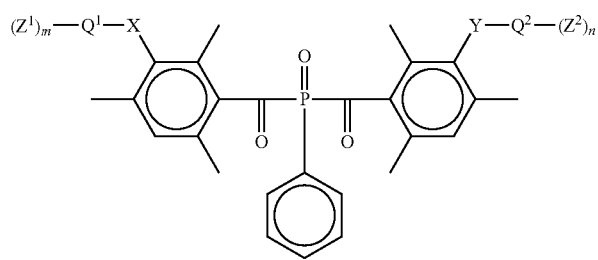
Formula III

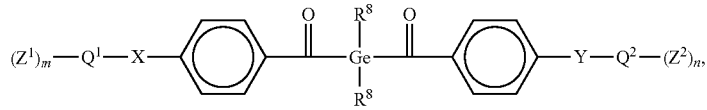
Formula IV wherein the given variables have the meanings defined above.

In this context those compounds of Formulae III and IV are preferred in which in each case independently of each other
one of $Z^1$ and $Z^2$ in each case independently represents a polymerizable group selected from $CH_2$=$CR^1$CO—O— and $CH_2$=$CR^1$—CO—$NR^2$— and the other of $Z^1$ and $Z^2$ in each case independently represents a polymerizable group selected from $CH_2$=$CR^1$—CO—O— and $CH_2$=$CR^1$—CO—$NR^2$— or preferably an adhesive group selected from —Si(OR)$_3$, —O—PO(OH)$_2$, —PO(OH)$_2$ and —SH,
$Q^1$ in each case independently is missing or represents an (m+1)-valent linear or branched aliphatic $C_1$-$C_{15}$ radical, preferably a $C_1$-$C_{10}$ radical, preferably a $C_1$-$C_8$ radical, in particular a $C_2$-$C_6$ radical and particularly preferably a $C_1$-$C_2$ radical, which can be interrupted by —O—, —CO—O—, —O—CO—, —CO—$NR^3$—, —$NR^3$—CO—, —O—CO—$NR^3$—, —$NR^3$—CO—O— or —$NR^3$—CO—$NR^3$—,
$Q^2$ in each case independently is missing or represents an (n+1)-valent linear or branched aliphatic $C_1$-$C_{15}$ radical, preferably a $C_1$-$C_{10}$ radical, preferably a $C_1$-$C_8$ radical, in particular a $C_2$-$C_6$ radical and particularly preferably a $C_2$-$C_3$ radical, which can be interrupted by —O—, —CO—O—, —O—CO—, —CO—$NR^3$—, —$NR^3$—CO—, —O—CO—$NR^3$—, —$NR^3$—CO—O— or —$NR^3$—CO—$NR^3$—,
X and Y in each case independently are missing or represent —O—, —CO—O—, —O—CO—, —CO—$NR^3$—, —$NR^3$—CO—, —O—CO—$NR^3$—, —$NR^3$—CO—O— or —$NR^3$—CO—$NR^3$—,
R in each case independently is $CH_3$ or $C_2H_5$,
$R^8$ in each case independently represents a $C_1$-$C_5$ alkyl radical and
m and n in each case independently are 1 or 2.

Compounds of Formulae III and IV are quite particularly preferred in which in each case independently of each other one of $Z^1$ and $Z^2$ in each case independently represents a polymerizable group selected from $CH_2$=$CR^1$—CO—O— and $CH_2$=$CR^1$—CO—$NR^2$— and the other of $Z^1$ and $Z^2$ in each case independently represents a polymerizable group selected from $CH_2$=$CR^1$—CO—O— and $CH_2$=$CR^1$—CO—$NR^2$— or preferably an adhesive group selected from —Si(OR)$_3$, —O—PO(OH)$_2$, —PO(OH)$_2$ and —SH,
$Q^1$ in each case independently is missing or represents an (m+1)-valent linear or branched aliphatic $C_1$-$C_8$ radical, in particular a $C_2$-$C_6$ radical and particularly preferably a $C_1$-$C_2$ radical which can be interrupted by —O—, —CO—O— or —O—CO—,
$Q^2$ in each case independently is missing or represents an (n+1)-valent linear or branched aliphatic $C_1$-$C_8$ radical, in particular a $C_2$-$C_6$ radical and particularly preferably a $C_2$-$C_3$ radical which can be interrupted by —O—, —CO—O— or —O—CO—,
X and Y in each case independently are missing or represent —O—, —CO—O— or —O—CO—,
R in each case independently is $CH_3$ or $C_2H_5$,
$R^8$ in each case independently represents a $C_1$-$C_4$ alkyl radical and
m and n in each case are 1.

Compounds in which all the variables each have one of the preferred meanings defined above are particularly preferred.

It was surprisingly found that after polymerization the dental restorative materials according to the invention which comprise at least one thermolabile and/or one photolabile polymerizable compound of Formula I and preferably at least one thermolabile polymerizable compound of Formula II and/or a photolabile polymerizable compound of Formulae III or IV on the one hand display excellent mechanical properties as well as an excellent adhesion to the tooth structure and dental ceramics and on the other hand can be easily debonded from the substrate by introducing heat (thermolabile bonds) or by irradiation by UV light or visible light (photolabile bonds).

The polymerizable Diels-Alder adducts of Formula II can be prepared easily. For example, suitably functionalized furan derivatives can be reacted with suitably N-functionalized maleinimides under reaction conditions customary for the Diels-Alder reaction and in particular at 80-120° C. e.g. in aromatic solvents and optionally accompanied by the addition of a suitable catalyst (for example Brønsted or Lewis acids) as well as a polymerization inhibitor (cf. team of authors, Organikum, Wiley-VCH, $21^{st}$ ed., Weinheim etc. 2001, 330 et seq.) to give a corresponding polymerizable Diels-Alder adduct:

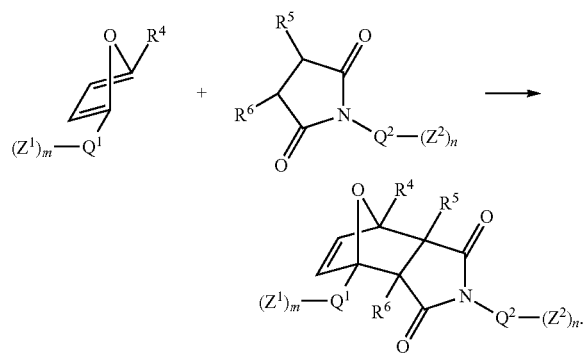

Specific example: Diels-Alder reaction of furfuryl methacrylate ($Z^1$=$CH_2$=$CR^1$—CO—O—, $Q^1$=—$CH_2$—, $R^1$=$CH_3$, $R^4$=H and m=1) and N-[3-(dihydroxyphosphoryl)propyl]-maleinimide ($Z^2$=—PO(OH)$_2$, $Q^2$=—(CH$_2$)$_3$—, $R^5$ and $R^6$=H and n=1):

Suitable starting materials for the synthesis of furan derivatives functionalized with polymerizable or strongly acidic groups are commercially available, for example furfural, furfuryl alcohol or pyromucic acid (cf. Ullmann's Encyclopedia of Industrial Chemistry, $5^{th}$ Ed., Vol. A 12, VCH, Weinheim etc. 1989, page 119 et seq.). Substituted furan derivatives can be prepared for example by Paal-Knorr synthesis by heating corresponding 1,4-diketo compounds (cf. W. Walter, W. Francke, Beyer-Walter Lehrbuch der Organischen Chemie, S. Hirzel Verlag, Stuttgart and Leipzig 2004, $24^{th}$ ed., page 769). Maleinimides functionalized with polymerizable or strongly acidic groups can be prepared most easily by reacting maleic anhydride with correspondingly functionalized amines.

The procedure for the synthesis of the Diels-Alder adducts of Formula II can also be stepwise, such that first a suitable Diels-Alder adduct is prepared from a suitably functionalized maleinimide and furan derivative and the introduction of the polymerizable or strongly acidic acid groups only takes place afterwards, wherein the syntheses are optionally carried out using protective groups. For example, the Diels-Alder adduct listed above by way of example can also be prepared with a polymerizable methacrylate group and a strongly acidic phosphonic acid group such that first the furfuryl alcohol, which is protected e.g. with a tetrahydropyranyl (THP) group, is converted to the Diels-Alder adduct with N-(3-bromopropyl)maleinimide. After introduction of the phosphonic acid group, e.g. via a Michaelis-Arbuzov reaction by reaction of the Diels-Alder adduct for instance with triethyl phosphite (P(OC$_2$H$_5$)$_3$), the THP protective group can be cleaved off, the OH group formed can be methacrylated e.g. with methacrylic anhydride (MAAH) and finally the phosphonic acid group can be hydrolytically released:

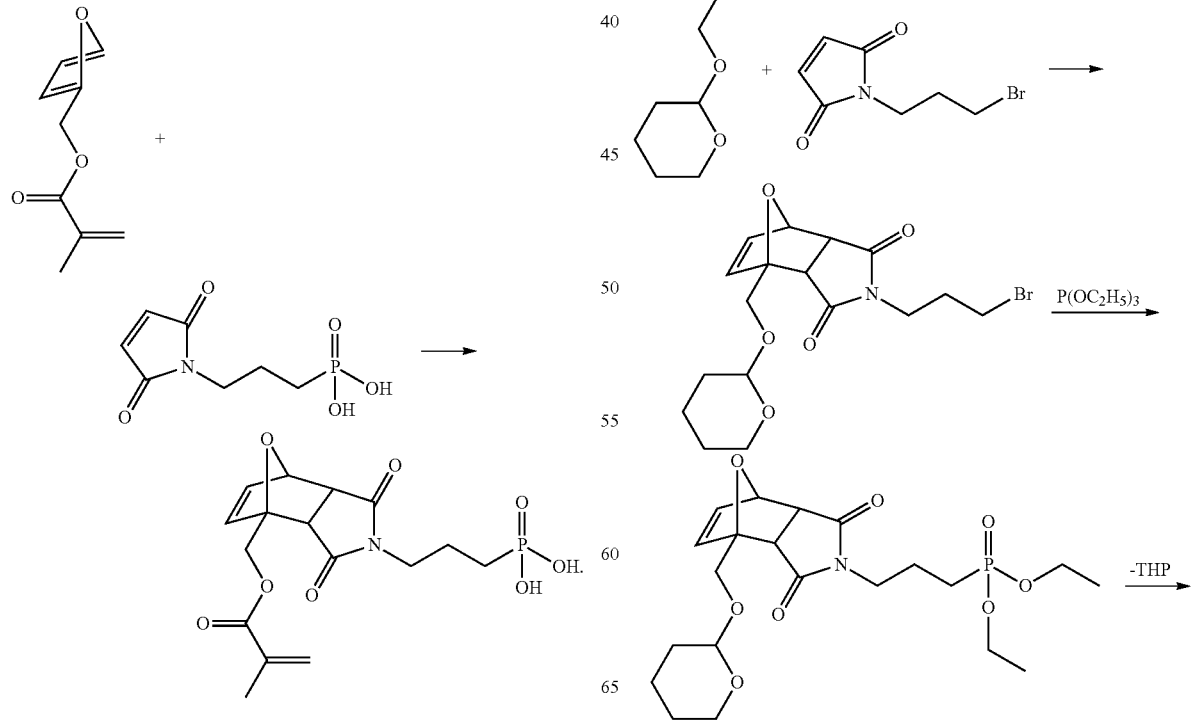

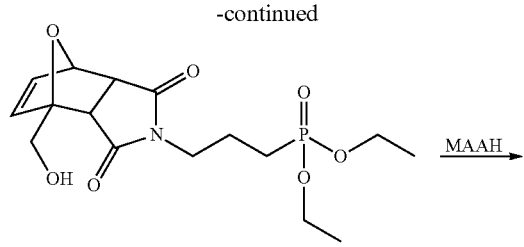
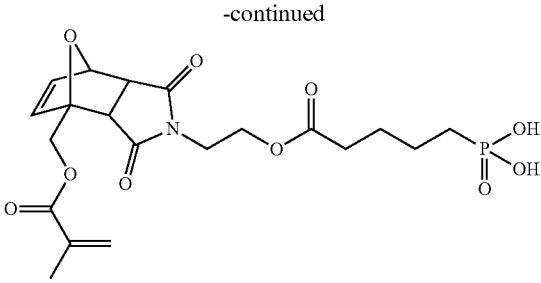
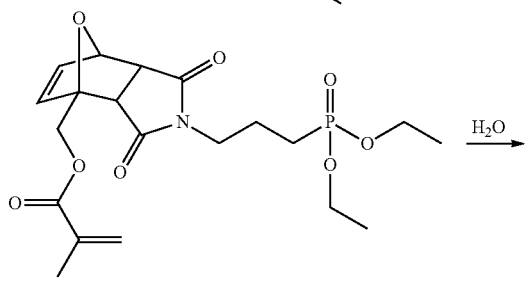
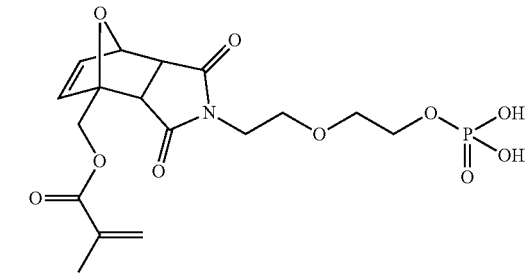
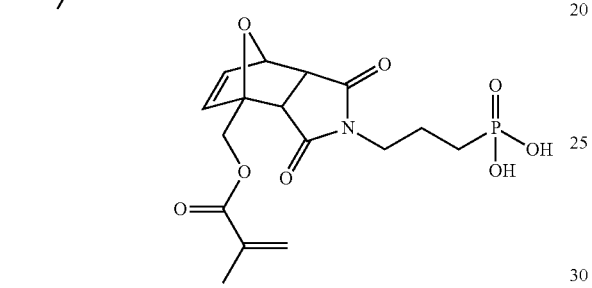
Examples of thermolabile Diels-Alder adducts of Formula II according to the invention are:
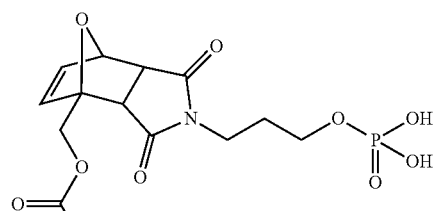
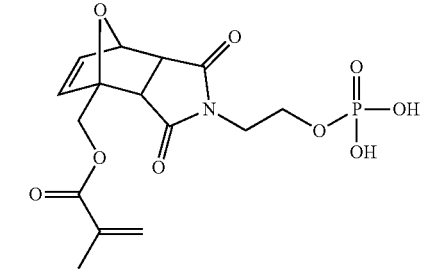
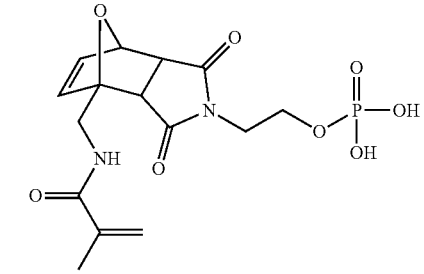
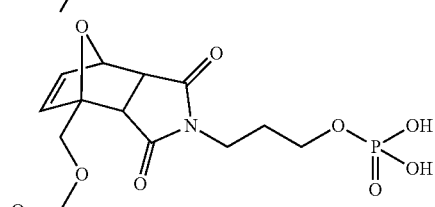
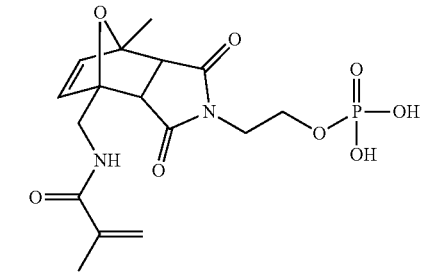
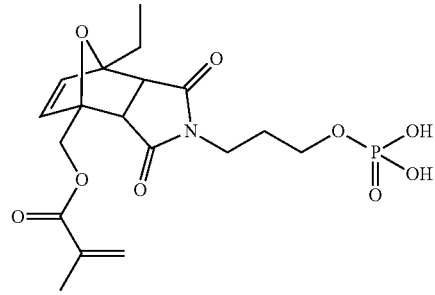
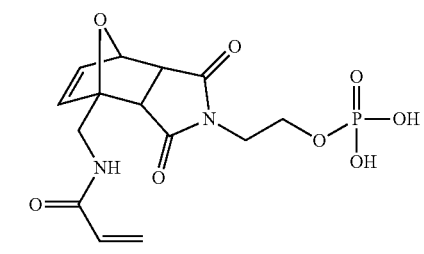

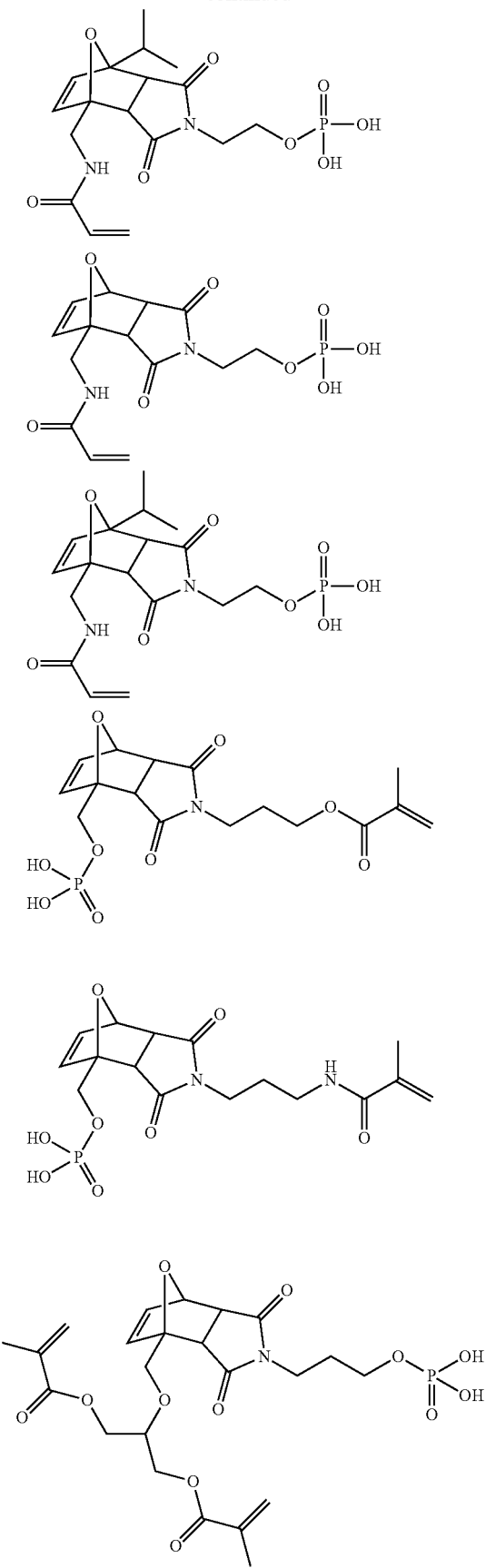
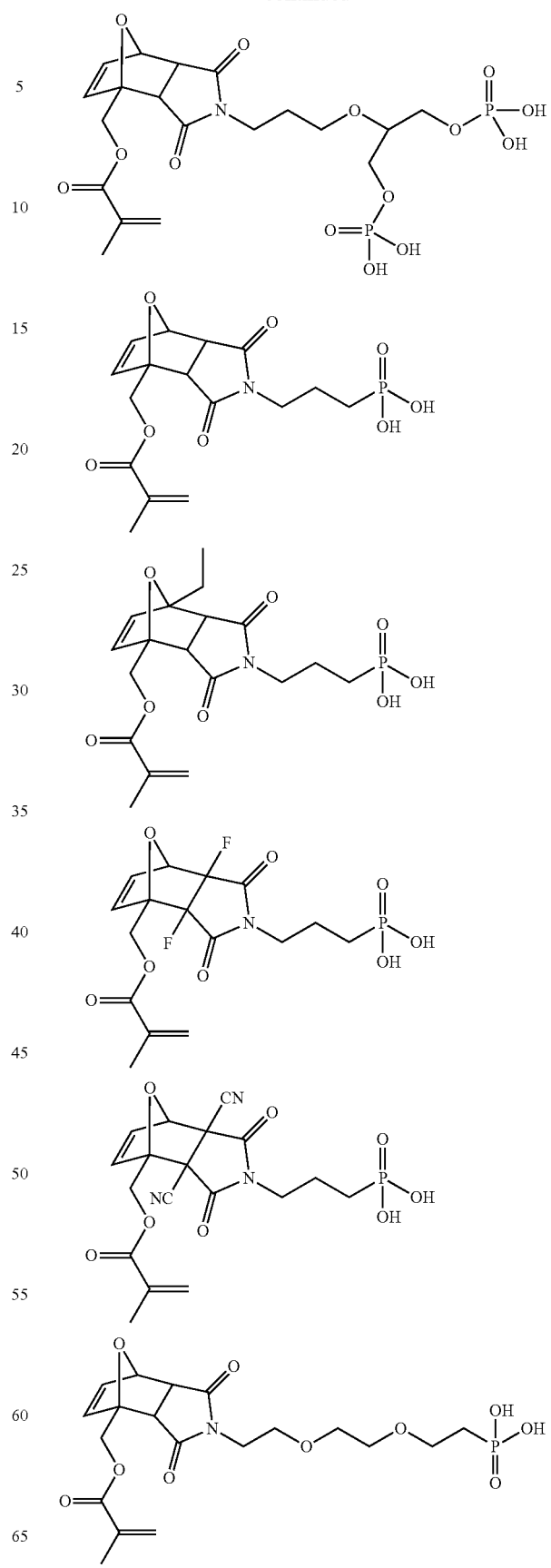

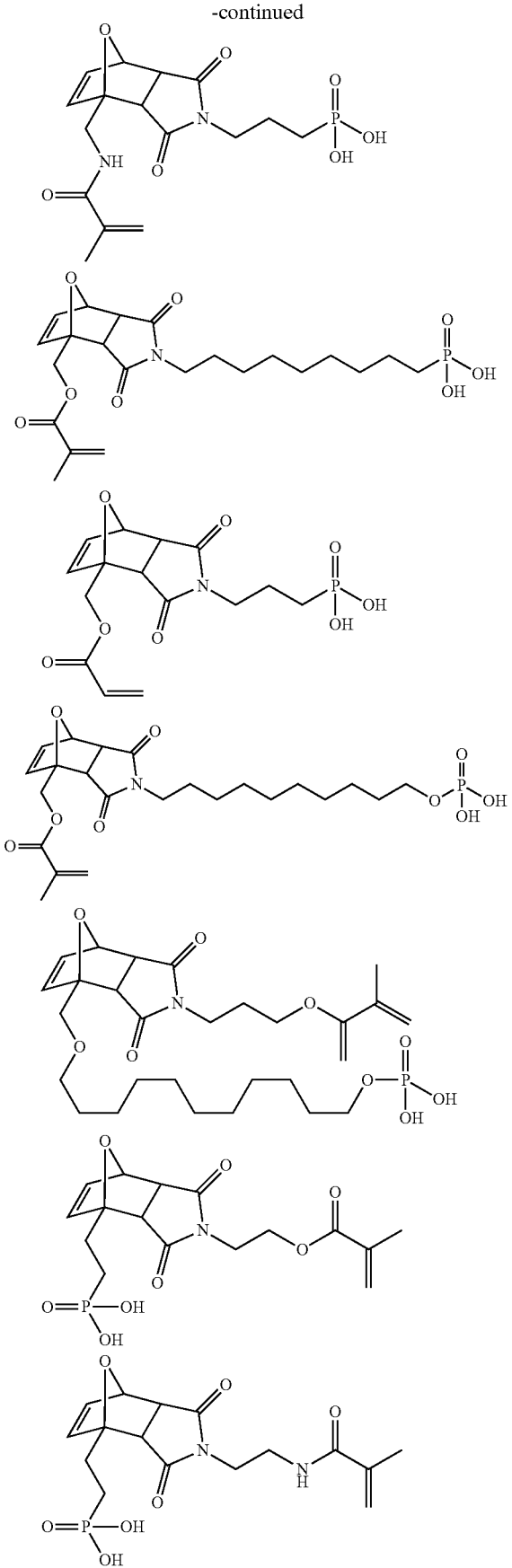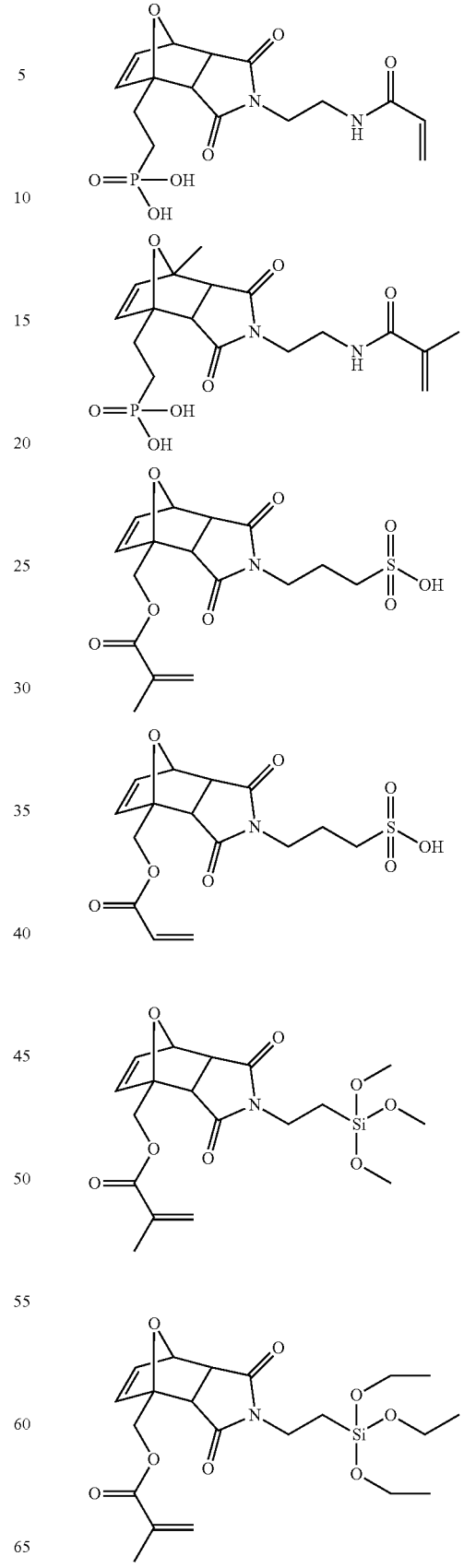

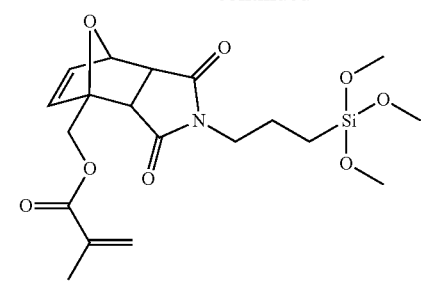
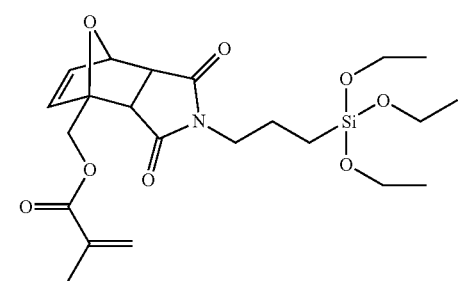
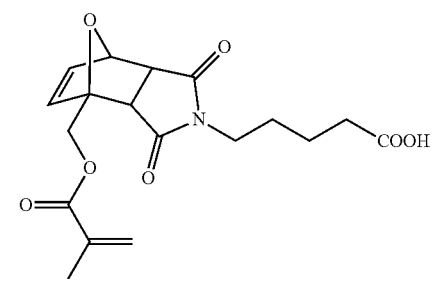
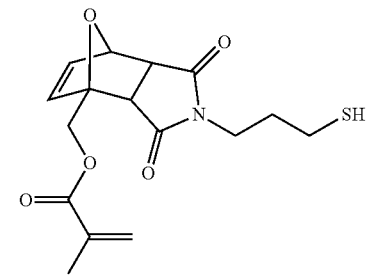
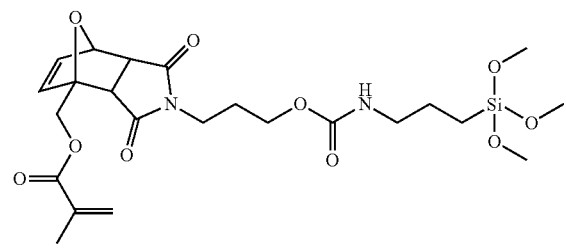
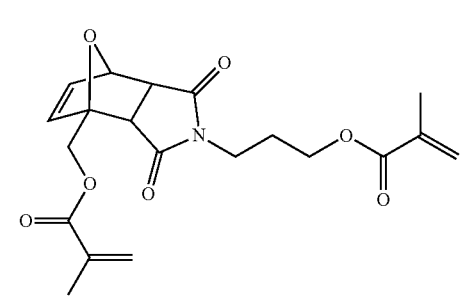
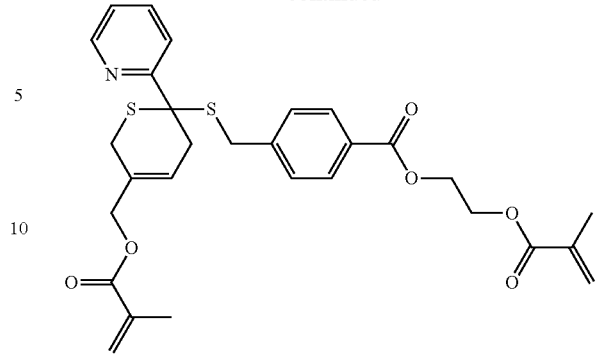
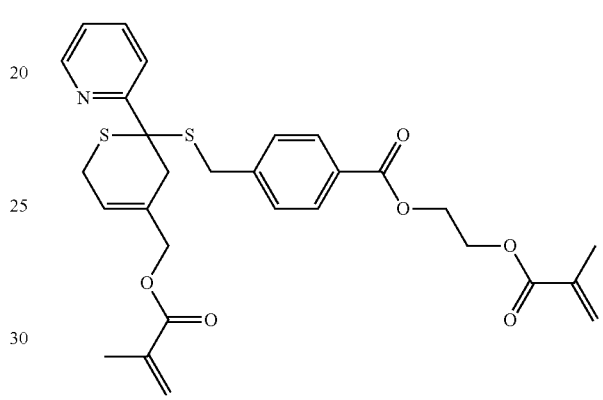
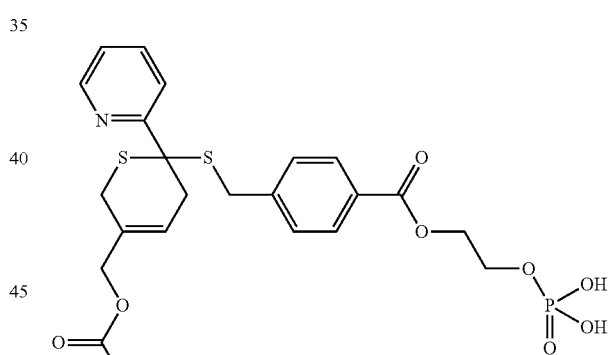
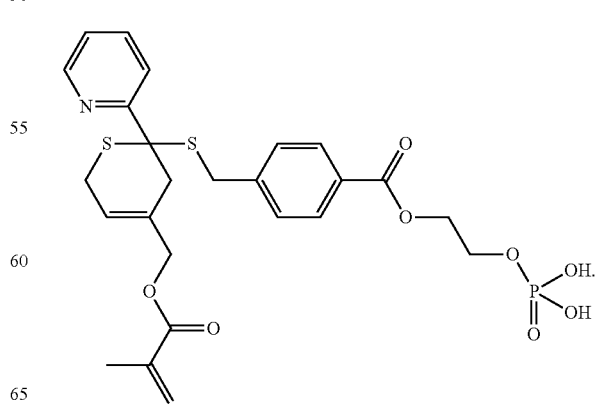

Examples of photolabile dibenzoylphenylphosphine oxides of Formula III according to the invention are:
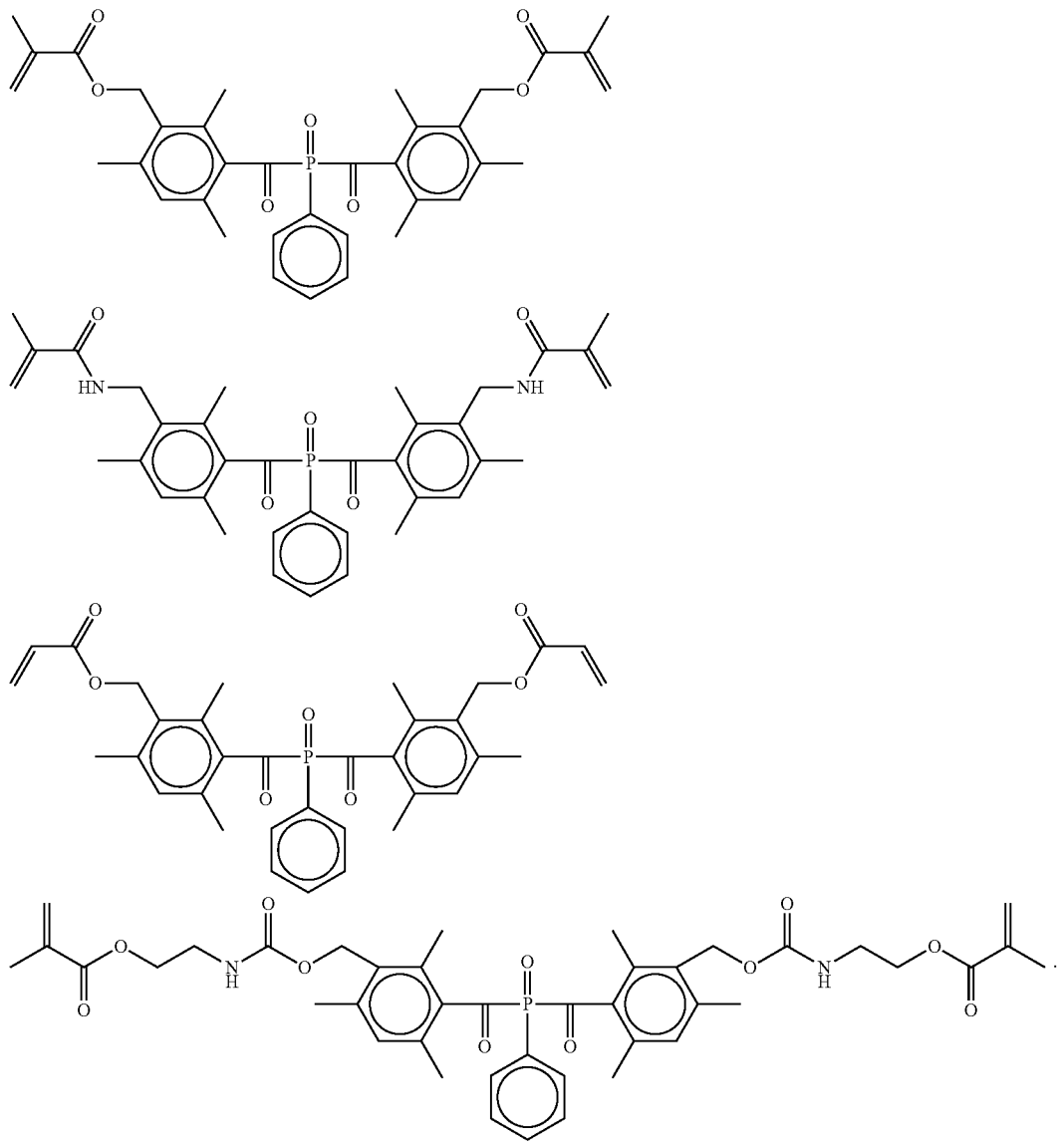
Examples of photolabile dialkyldibenzoyl germanium derivatives of Formula IV according to the invention are:
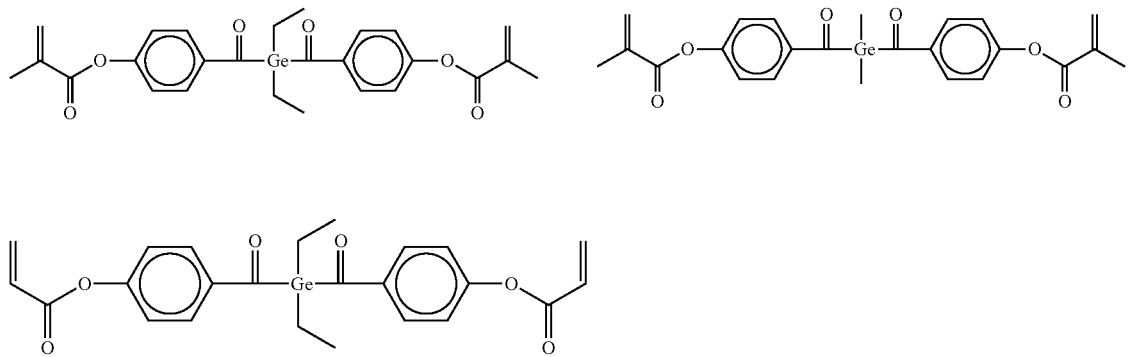

-continued

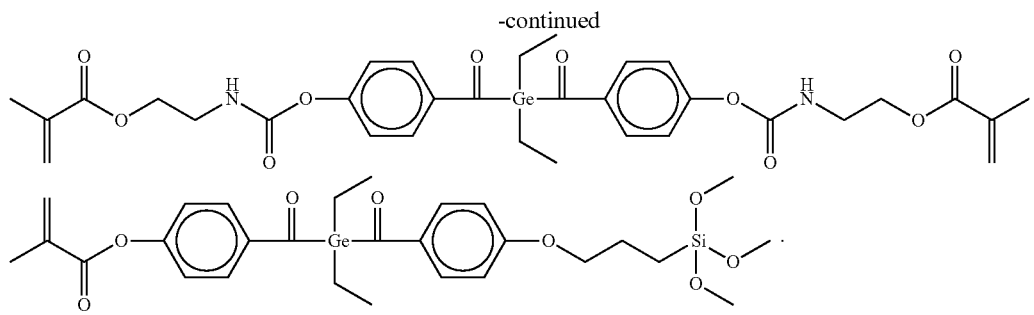

The dental materials according to the invention preferably comprise, in addition to the thermolabile or photolabile polymerizable compound of Formula I, one or more additional radically polymerizable monomers (comonomers), in particular mono- or polyfunctional (meth)acrylic acid derivatives. By monofunctional (meth)acrylic acid derivatives are meant compounds with one (meth)acrylic acid group, by polyfunctional (meth)acrylic acid derivatives are meant compounds with two or more, preferably 2 to 4, (meth)acrylic acid groups. Polyfunctional monomers have a cross-linking effect.

Preferred mono- or polyfunctional (meth)acrylic acid derivatives according to the invention are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate (HEMA) and 2,2,4-trimethylhexamethylene diisocyanate), di-, tri- or tetraethylene glycol di(meth)acrylate, trimethylolpropane tri(meth)acrylate, pentaerythritol tetra(meth)-acrylate, glycerol di(meth)acrylate, 1,4-butanediol di(meth)acrylate, 1,10-decanediol di(meth)acrylate and 1,12-dodecanediol di(meth)-acrylate.

Particularly preferred mono or polyfunctional (meth)acrylic acid derivatives are N-mono- or disubstituted acrylamides such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxyethyl)methacrylamide as well as N-vinylpyrrolidone and allyl ether. These monomers are characterized by a high hydrolysis stability and are particularly suitable as diluting monomers because of their relatively low viscosity.

Preferred polyfunctional (meth)acrylic acid derivatives with high hydrolysis stability are cross-linking pyrrolidones such as 1,6-bis(3-vinyl-2-pyrrolidonyl)-hexane, bisacrylamides such as methylene or ethylene bisacrylamide and bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by reacting the corresponding diamines with (meth)acrylic acid chloride.

Thermolabile cross-linking monomers are also particularly suitable according to the invention as comonomers. Thermolabile cross-linking monomers have at least one thermolabile group between two polymerizable groups. Examples are polyfunctional (meth)acrylates or (meth)acrylamides with at least one thermolabile group between two (meth)acrylic groups. In principle, coming into consideration as thermolabile groups are the same groups as are defined above for the compounds of Formula I, and in particular thermolabile cycloaddition adducts such as Diels-Alder adducts, hetero-Diels-Alder adducts as well as thermolabile alkoxyamine, oxime-ester, oxime-urethane or azo groups. Examples are Diels-Alder adducts such as the Diels-Alder adduct from furfuryl methacrylate and N-(3-(methacryloyloxy)propyl)-maleinimide, the reaction products of N-hydroxy-(meth)acrylamide with di- or triisocyanates such as hexamethylene-1,6-diisocyanate (HDI), 2,2,4-trimethylhexamethylene-1,6-diisocyanate or the HDI trimer, as well as products which are obtained by stoichiometric reaction of di- or triisocyanates with 1-hydroxymethylacrylic esters such as 1-hydroxymethyl ethyl acrylate or with β-keto ester (meth)acrylates such as 2-acetoacetoxyethyl methacrylate. Gas-releasing thermolabile cross-linking monomers are also particularly suitable. Examples are the esterification products of azobis(4-cyanovaleric acid) with hydroxyalkyl (meth)acrylates such as hydroxyethyl (meth)acrylate or hydroxypropyl (meth)acrylate or with N-(hydroxyalkyl) (meth)acrylamides such as N-(5-hydroxypentyl) methacrylamide or N-methyl-N-(2-hydroxyethyl)acrylamide.

In addition to the thermolabile or photolabile polymerizable compound of Formula I and optionally the above-named comonomers, the dental restorative materials according to the invention can preferably also comprise radically polymerizable, acid group-containing monomers (adhesive monomers). Preferred acid groups are carboxylic acid groups, phosphonic acid groups, phosphoric acid groups and sulphonic acid groups.

Preferred monomers with polymerizable carboxylic acids are maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

Preferred monomers with polymerizable phosphonic acid groups are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid, 2-[4-(dihydroxyphosphoryl)-2-oxa-butyl]-acrylic acid ethyl and -2,4,6-trimethylphenyl ester.

Preferred monomers with polymerizable phosphoric acid groups are 2-methacryloyloxypropyl mono- or dihydrogen phosphate, 2-methacryloyloxyethyl mono- or dihydrogen phosphate, 2-methacryloyloxyethyl-phenyl hydrogen phosphate, dipentaerythritolpentamethacryloyloxy phosphate, 10-methacryloyloxydecyl dihydrogen phosphate, phosphoric acid mono-(1-acryloyl-piperidin-4-yl)-ester, 6-(methacrylamido)hexyl dihydrogen phosphate and 1,3-bis-(N-acryloyl-N-propyl-amino)-propan-2-yl-dihydrogen phosphate.

Preferred monomers with polymerizable sulphonic acid groups are vinylsulphonic acid, 4-vinylphenylsulphonic acid and 3-(methacryl-amido)propylsulphonic acid.

Preferably, mixtures of the above-named monomers are used. Based on the total weight of the monomer mixture, preferred monomer mixtures comprise:

1 to 90 wt.-%, preferably 5 to 80 wt.-%, particularly preferably 5 to 70 compound of Formula I and in particular of Formula II, III and/or IV, 0 to 70 wt.-%, preferably 1 to 60 wt.-%, particularly preferably 5 to 50 and quite particularly preferably 10 to 30 wt.-% comonomer and in particular mono- and/or polyfunctional (meth)acrylates, 0 to 70 wt.-%, preferably 1 to 60 wt.-% and particularly preferably 5 to 50 wt.-% thermolabile cross-linking monomer and 0 to 40 wt.-%, preferably 1 to 30 wt.-% and particularly preferably 5 to 20 wt.-% adhesive monomer.

Particularly preferred monomer mixtures (in each case based on the total weight of the monomer mixture) are given in the following table:

| Component (wt.-%) | A | B | C | D | E | F |
|---|---|---|---|---|---|---|
| Compound of Formula I, in particular of Formula II, III and/or IV | 1-90 | 5-80 | 5-70 | 5-70 | 5-70 | 5-70 |
| Comonomer, in particular mono- and/or polyfunctional (meth)acrylate | 0-70 | 0-60 | 1-60 | 5-60 | 5-50 | 0-30 |
| Thermolabile cross-linking monomer | 0-70 | 0-50 | 0-50 | 5-50 | 5-50 | 5-50 |
| Adhesive monomer | 0-40 | 0-30 | 0-30 | 0-20 | 0-20 | 0-30 |

Moreover, the dental restorative materials according to the invention preferably also comprise an initiator for radical polymerization.

Preferably, benzophenone, benzoin and their derivatives or α-diketones or their derivatives, such as 9,10-phenanthrenequinone, 1-phenyl-propane-1,2-dione, diacetyl or 4,4'-dichlorobenzil are used to initiate radical photopolymerization, in particular in the case of thermolabile compounds of Formula I. Camphorquinone and 2,2-dimethoxy-2-phenyl-acetophenone are particularly preferably used, and quite particularly preferably α-diketones combined with amines, such as 4-(dimethylamino)-benzoate, N,N-dimethylaminoethyl methacrylate, N,N-dimethyl-sym.-xylidine or triethanolamine as reductants. Norrish type I photoinitiators, in particular acyl or bisacylphosphine oxides, monoacyltrialkyl- or diacyldialkylgermanium compounds, such as benzoyltrimethylgermanium, dibenzoyldiethylgermanium or bis-(4-methoxybenzoyl)diethylgermanium are also particularly suitable. Mixtures of the different photoinitiators can also be used, such as for example dibenzoyldiethylgermanium combined with camphorquinone and 4-dimethylaminobenzoic acid ethyl ester.

Preferably, redox-initiator combinations, such as for example combinations of benzoyl peroxide with N,N-dimethyl-sym.-xylidine or N,N-dimethyl-p-toluidine, are used as initiators for a polymerization carried out at room temperature, in particular in the case of photolabile compounds of Formula I. Furthermore, redox systems consisting of peroxides and reductants such as e.g. ascorbic acid, barbiturates or sulphinic acids, are also particularly suitable.

The dental restorative materials according to the invention can also comprise a thermally gas-releasing additive. Suitable gas-releasing additives are e.g. azo compounds such as azodicarbonamide, 2,2'-azobisisobutyronitrile or 2,2'-azobis (4-cyanopentanoic acid), N-nitroso compounds, hydrazides such as benzenesulphonyl hydrazide, peroxides such as dicumol peroxide or acetone dicarboxylic acid. Examples of such compounds are described for instance in St. Quinn, *Plastics, Additives & Compounding* 2001, 3, 16-21. The decomposition temperature, for example in the case of azo compounds, can be set in a manner known per se by the substituent pattern (cf. D. Braun, R. Jakobi, *Monatshefte Chemie* 1982, 113, 1403-1414).

Furthermore, the dental restorative materials according to the invention can comprise an additive which can convert radiated electromagnetic radiation into heat. Such so-called radiation-to-heat converters are organic, inorganic or organometallic substances or hybrid components which are capable of converting UV, NIR or IR radiation, visible light, microwave or radiowave radiation into heat in order to cleave thermolabile groups. Examples of this are dyes and pigments that absorb UV, NIR or IR radiation. Examples of dyes that absorb in the IR range are azo, methine, anthraquinone or porphyrin dyes. Examples of pigments that absorb NIR radiation are antimony and indium tin oxide, phthalocyanine pigments, soot, Ni and Pt dithiolene complexes. Examples of compounds that absorb in the UV range are benzotriazoles, triazines, benzophenones, cyanoacrylates, salicylic acid derivatives and hindered amine light stabilizers (HALS). Examples of additives that absorb in the frequency range of microwaves (1 to 300 GHz) or radiowaves (10 kHz to 1 GHz) are ferromagnetic ceramic substances, so-called ferrites, which are composed of the iron oxides haematite ($Fe_2O_3$) or magnetite ($Fe_3O_4$) and further oxides for example of the metals Zn, Mn, or Ni and are commercially available as powders.

The dental restorative materials according to the invention furthermore preferably also comprise organic or inorganic filler particles to improve the mechanical properties or to adjust the viscosity. Preferred inorganic particulate fillers are amorphous spherical materials based on oxides, such as $ZrO_2$ and $TiO_2$, or mixed oxides of $SiO_2$, $ZrO_2$ and/or $TiO_2$ with an average particle size of from 0.005 to 2 μm, preferably 0.1 to 1 μm, nanoparticulate or microfine fillers such as pyrogenic silicic acid or precipitated silica with an average particle size of from 5 to 200 nm, preferably 10 to 100 nm, minifillers such as quartz, glass ceramic or glass powders with an average particle size of from 0.01 to 10 μm, preferably 0.1 to 1 μm, as well as X-ray-opaque fillers such as ytterbium trifluoride or nanoparticulate tantalum(V) oxide or barium sulphate with an average particle size of from 10 to 1000 nm, preferably 100 to 300 nm.

Moreover, the dental restorative materials according to the invention can comprise further additives, in particular solvents such as water or ethanol or corresponding solvent mixtures as well as for example stabilizers, flavourings, dyes, microbiocidal active ingredients, fluoride ion-releasing additives, optical brighteners or plasticizers.

Dental restorative materials based on a thermolabile or photolabile polymerizable compound of Formula I and in particular of Formula II, III and/or IV which comprise the following components are particularly preferred:

a) 0.1 to 50 wt.-%, in particular 1 to 40 wt.-%, preferably 2 to 30 wt.-% and particularly preferably 5 to 30 wt.-% compound of Formula I and in particular of Formula II, III and/or IV,
b) 0.01 to 10 wt.-%, preferably 0.1 to 3.0 wt.-% and particularly preferably 0.2 to 2 wt.-% initiator,
c) 0 to 80 wt.-%, preferably 1 to 60 wt.-% and particularly preferably 5 to 50 wt.-% comonomer,
d) 0 to 30 wt.-%, preferably 0.5 to 15 wt.-% and particularly preferably 1 to 5 wt.-% adhesive monomer,
e) 0 to 80 wt.-% filler,
f) 0 to 70 wt.-% solvent.

The preferred filler content depends on the desired use. Adhesives preferably comprise 0 to 20 wt.-% and cements and composites preferably comprise 20 to 80 wt.-% filler.

The same also applies to the solvent content. Adhesives preferably comprise 0 to 60 wt.-% and particularly preferably 1 to 50 wt.-% solvent. Dental materials which comprise water as solvent are preferred. Dental materials which comprise 0 to 20 wt.-% and in particular 1 to 10 wt.-% water are particularly preferred.

The debonding properties of the dental restorative materials according to the invention can be influenced in a targeted manner by the composition of the materials. The adjustment of a composition suitable for a particular purpose belongs to the general knowledge and abilities of a person skilled in the art. Thus, the ability to debond on demand by heating increases with the concentration used of thermolabile or photolabile components, i.e. in particular the thermolabile or photolabile polymerizable compound of Formula I as well as optionally the thermolabile cross-linking monomers and gas-releasing additives. Furthermore, the debonding properties can also be varied by the selection of the comonomers, wherein the cross-linking density and thus also the strength and the elastic modulus can be varied with the proportion of cross-linking monomers or by addition of monofunctional monomers.

The dental materials according to the invention based on the thermolabile or photolabile polymerizable compound of Formula I and preferably of Formula II, III and/or IV can be used in particular to reversibly attach for example brackets, crowns or veneers. Preferably, a bond is initially formed by curing materials (adhesive or cement) based on the thermolabile or photolabile polymerizable compound of Formula I. For debonding, the adhesively bonded parts must be heated briefly to a temperature which lies above the temperature at which the cleavage of the thermolabile bonds sets in, or irradiated with light of a suitable wavelength. A targeted introduction of energy can take place for example via an IR radiation source or a laser. Moreover, an inductive heating can be achieved by the action of an alternating magnetic field when ferromagnetic particles such as for example ferromagnetic nanoparticles are incorporated into the dental materials according to the invention.

A subject of the invention is also the use of a thermolabile or photolabile polymerizable compound of Formula I and in particular of Formula II, III and/or IV for the preparation of dental restorative materials, preferably adhesives or cements, particularly preferably self-etching adhesives or cements.

The invention is explained in more detail below by means of examples.

EXAMPLES

Example 1

Synthesis of methacrylic acid-3,5-dioxo-4-(3-phosphonooxypropyl)-10-oxa-4-aza-tricyclo [5.2.1.0$^{2,6}$]dec-8-en-1-ylmethyl ester (MATPA)

Step 1: 4,10-Dioxa-tricyclo[5.2.1.0$^{2,6}$]dec-8-ene-3, 5-dione

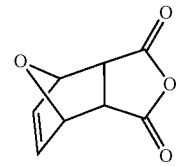 [SMILES: O=C1OC(=O)C2C3C=CC(O3)C12]

A solution of maleic anhydride (98.06 g, 1.0 mol) and furan (102.12 g, 1.5 mol) in acetonitrile (200 ml) was stirred for 96 h at room temperature. The precipitate formed was filtered off, washed with acetonitrile (100 ml) and dried in a vacuum drying oven (125 mbar, 50° C.). 123.30 g (740 mmol, 74% yield) of a white solid was obtained.

$^1$H-NMR (DMSO-d$_6$, 400 MHz): δ=3.31 (s, 2H), 5.35 (s, 2H), 6.58 (s, 2H).

$^{13}$C-NMR (DMSO-d$_6$, 100 MHz): δ=49.0, 81.6, 136.8, 171.5.

Step 2: 4-(3-Hydroxy-propyl)-10-oxa-4-aza-tricyclo [5.2.1.0$^{2,6}$]dec-8-ene-3,5-dione

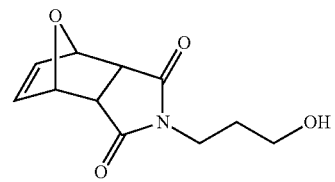 [SMILES: O=C1C2C3C=CC(O3)C2C(=O)N1CCCO]

A solution of 3-amino-1-propanol (15.02 g, 200 mmol) in methanol (30 ml) was added dropwise to a suspension of 4,10-dioxa-tricyclo[5.2.1.0$^{2,6}$]dec-8-ene-3,5-dione (33.23 g, 200 mmol) in methanol (70 ml). The reaction mixture was then heated under reflux. After 24 h, the solution was concentrated on a rotary evaporator. The yellowish solid was dissolved in water (100 ml) and extracted with dichloromethane (3×200 ml). The combined organic phases were dried over Na$_2$SO$_4$, filtered, concentrated on the rotary evaporator and dried under fine vacuum. 25.40 g (114 mmol, 57% yield) of a white solid was obtained.

$^1$H-NMR (DMSO-d$_6$, 400 MHz): δ=1.59 (m, 2H), 2.91 (s, 2H), 3.38 (m, 4H), 4.45 (br s, 1H), 5.12 (s, 2H), 6.55 (s, 2H).
$^{13}$C-NMR (DMSO-d$_6$, 100 MHz): δ=30.5, 35.5, 47.0, 58.3, 80.3, 136.4, 176.4.

Step 3: 1-(3-Hydroxy-propyl)-pyrrole-2,5-dione

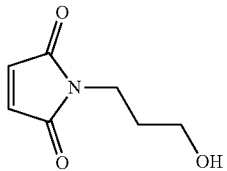 [SMILES: O=C1C=CC(=O)N1CCCO]

A solution of 4-(3-hydroxy-propyl)-10-oxa-4-aza-tricyclo[5.2.1.0$^{2,6}$]dec-8-ene-3,5-dione (17.80 g, 79.8 mmol) in toluene (300 ml) was heated under reflux for 16 h. The solution was concentrated on the rotary evaporator and the residue dried under fine vacuum. 11.92 g (76.8 mmol, 96% yield) of a white solid was obtained.

$^1$H-NMR (DMSO-d$_6$, 400 MHz): δ=1.65 (m, 2H), 3.40 (t, 2H; J=6.2 Hz), 3.47 (t, 2H; J=7.4 Hz), 4.48 (br s, 1H), 6.99 (s, 2H).

$^{13}$C-NMR (DMSO-d$_6$, 100 MHz): δ=31.2, 34.7, 58.4, 134.4, 171.0.

Step 4: Methacrylic acid-4-(3-hydroxypropyl)-3,5-dioxo-10-oxa-4-aza-tricyclo[5.2.1.0$^{2,6}$]dec-8-en-1-ylmethyl ester

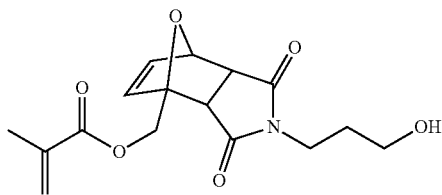 [SMILES: C=C(C)C(=O)OCC12C=CC(O1)C1C(=O)N(CCCO)C(=O)C12]

1-(3-Hydroxy-propyl)-pyrrole-2,5-dione (5.17 g, 33.3 mmol), furfuryl methacrylate (5.65 g, 34.0 mmol) and BHT (10 mg) were dissolved in benzene (60 ml). The solution was heated under reflux accompanied by the introduction of a light air stream. The solvent was distilled off after 20 h. The brownish oil was purified by means of column chromatography (SiO$_2$, ethyl acetate). 2.84 g (8.8 mmol, 27% yield, mixture of exo and endo isomer) of a yellowish oil was obtained.

$^1$H-NMR (DMSO-d$_6$, 400 MHz): δ (endo isomer)=1.55-1.64 (m, 2H), 1.88 (s, 3H), 3.01-3.05 (d, 1H; J=6.4 Hz), 3.09 (d, 1H; J=6.4 Hz), 3.32-3.49 (m, 4H), 4.41 (d, 1H; J=12.8 Hz), 4.45-4.48 (m, 1H), 4.78-4.84 (m, 1H), 5.15 (d, 1H; J=1.5 Hz), 5.68-5.70 (m, 1H), 6.00-6.03 (m, 1H), 6.47-6.52 (m, 1H), 6.58-6.64 (m, 1H).

$^{13}$C-NMR (DMSO-d$_6$, 100 MHz): δ (endo isomer)=17.8, 30.5, 35.6, 48.1, 49.6, 58.2, 61.7, 80.5, 88.8, 126.2, 135.4, 136.7, 137.3, 166.1, 174.7, 176.0.

Step 5: Methacrylic acid-3,5-dioxo-4-(3-phosphonooxypropyl)-10-oxa-4-aza-tricyclo[5.2.1.0$^{2,6}$]dec-8-en-1-ylmethyl ester (MATPA)

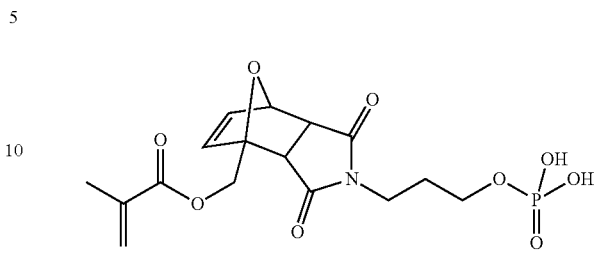

A solution of methacrylic acid-4-(3-hydroxypropyl)-3,5-dioxo-10-oxa-4-aza-tricyclo[5.2.1.0$^{2,6}$]dec-8-en-1-ylmethyl ester (2.6 g, 8.2 mmol), BHT (10 mg) and triethylamine (910 mg, 9.0 mmol) in tetrahydrofuran (20 ml) was added dropwise to a solution of phosphoroxychloride (1.39 g, 9.0 mmol) in tetrahydrofuran (30 ml) at −5° C. After addition was complete, the suspension was stirred for 3 h at −5° C. and then water (2 ml) was added dropwise. The suspension was stirred for a further 30 min at −5° C. and the precipitate was then filtered off cold. The yellowish filtrate was washed with saturated aqueous NaCl solution (3×30 ml). The combined aqueous phases were re-extracted with tetrahydrofuran (2×30 ml). The combined organic phases were dried over Na$_2$SO$_4$, filtered and concentrated on the rotary evaporator. The brownish oil had acetonitrile (2×50 ml) added to it to remove water and was concentrated on the rotary evaporator. The residue had diethyl ether (50 ml) added to it and was stirred at room temperature. The solvent was decanted off after 1 h. The brown oil was dried on the rotary evaporator and under fine vacuum. 2.46 g (6.1 mmol, 75% yield, mixture of exo and endo isomer) of a brownish resin was obtained.

$^1$H-NMR (DMSO-d$_6$, 400 MHz): δ (endo isomer)=1.73-1.82 (m, 2H), 1.87 (s, 3H), 3.03 (d, 1H; J=6.5 Hz), 3.10 (d, 1H; J=6.5 Hz), 3.42-3.48 (m, 2H), 3.76-3.84 (m, 2H), 4.41 (d, 1H; J=12.5 Hz), 4.84 (d, 1H; J=12.5 Hz), 5.15 (s, 1H), 5.69 (s, 1H), 6.01 (s, 1H), 6.50 (d, 1H; J=5.7 Hz), 6.59-6.63 (m, 1H), 6.94 (br, 2H).

$^{13}$C-NMR (DMSO-d$_6$, 100 MHz): δ (endo isomer)=17.8, 28.2 (d, J=7 Hz), 35.2, 48.2, 49.7, 61.6, 63.0 (d, J=5 Hz), 80.4, 88.8, 126.2, 135.4, 136.7, 137.3, 166.1, 174.7, 176.0.

$^{31}$P-NMR (DMSO-d$_6$, 162 MHz): δ=−1.3.

Example 2

Synthesis of methacrylic acid-3-(3,5-dioxo-1-phosphonooxymethyl-10-oxa-4-aza-tricyclo[5.2.1.0$^{2,6}$]dec-8-en-4-yl)-propyl ester

Step 1: Methacrylic acid-3-(2,5-dioxo-2,5-dihydropyrrol-1-yl)-propyl ester

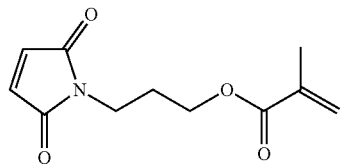 [SMILES: C=C(C)C(=O)OCCCN1C(=O)C=CC1=O]

1-(3-Hydroxypropyl)-pyrrole-2,5-dione (5.36 g, 34.5 mmol), triethylamine (3.85 g, 38.0 mmol) and N,N-dimethylaminopyridine (120 mg, 1.0 mmol) were dissolved in dichloromethane (80 ml). A solution of methacrylic anhydride (5.86 g, 38.0 mmol) and BHT (10 mg) in dichloromethane (20 ml) was added dropwise at 0° C., and the reaction mixture was then stirred for 2 h at 0° C. and 22 h at room temperature. The reaction solution was washed with water (3×50 ml). The combined aqueous phases were re-extracted with dichloromethane (50 ml). The combined organic phases were dried over $Na_2SO_4$, filtered and concentrated on the rotary evaporator. The crude product was purified by means of column chromatography ($SiO_2$, n-hexane/ethyl acetate 1:1). 2.81 g (12.5 mmol, 35% yield) of a yellowish oil was obtained.

$^1$H-NMR (CDCl$_3$, 400 MHz): δ=1.95 (2, 3H), 1.97-2.04 (m, 2H), 3.66 (t, 2H; J=6.9 Hz), 4.15 (t, 2H; J=6.2 Hz), 5.57 (m, 1H), 6.12 (s, 1H), 6.72 (s, 2H).

$^{13}$C-NMR (CDCl$_3$, 100 MHz): δ=18.3, 27.6, 34.9, 61.8, 125.6, 134.2, 126.2, 167.2, 170.6.

Step 2: Methacrylic acid-3-(1-hydroxymethyl-3,5-dioxo-10-oxa-4-aza-tricyclo[5.2.1.0$^{2,6}$]dec-8-en-4-yl)-propyl ester

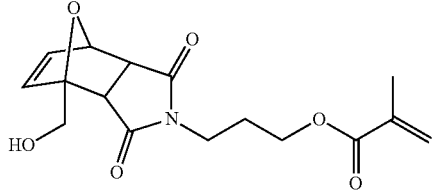 [SMILES: C=C(C)C(=O)OCCCN1C(=O)C2C3C=CC(CO)(O3)C2C1=O]

Methacrylic acid-3-(2,5-dioxo-2,5-dihydro-pyrrol-1-yl)-propyl ester (2.71 g, 12.1 mmol), furfuryl alcohol (1.28 g, 13.0 mmol) and BHT (10 mg) were dissolved in benzene (40 ml). The solution was heated under reflux accompanied by the introduction of a light air stream. The solvent was distilled off after 20 h. The brownish oil obtained as crude product was purified by means of column chromatography (SiO$_2$, ethyl acetate). 3.10 g (9.6 mmol, 80% yield, mixture of exo and endo isomer) of a yellow oil was obtained.

$^1$H-NMR (CDCl$_3$, 400 MHz): δ=1.78-1.89 (m, 0.4H; exo), 1.93-2.02 (m, 5.8H; exo/endo), 2.94-3.02 (m, 3H; endo), 3.43-3.48 (m, 0.6H; exo), 3.55-3.69 (m, 2.2H; exo/endo), 4.05-4.14 (m, 4.4H; exo/endo), 4.15-4.22 (m, 0.2H; exo), 4.25-4.31 (m, 0.2H; exo), 5.25 (m, 1H; endo), 5.28-5.32 (m, 0.2H; exo), 5.57-5.60 (m, 1.2H; exo/endo), 6.10-6.12 (m, 0.2H; endo), 6.12-6.14 (m, 1H; endo), 6.35-6.38 (m, 0.2H; exo), 6.46-6.49 (m, 0.2H; exo), 6.52-6.56 (m, 1H; endo), 6.59-6.62 (m, 1H; endo).

$^{13}$C-NMR (CDCl$_3$, 100 MHz): δ=18.3, 26.6 (endo), 26.7 (exo), 35.5 (exo), 35.8 (endo), 46.0 (exo), 48.1 (endo), 49.9, 60.7 (endo), 61.3 (exo), 61.4 (endo), 61.6 (exo), 79.5 (exo), 80.9 (endo), 91.5 (endo), 92.1 (exo), 125.7 (endo), 125.8 (exo), 134.9 (exo), 135.7 (exo), 136.1 (exo), 136.2 (exo), 137.0 (endo), 138.3 (endo), 167.2 (exo), 167.3 (exo), 174.7 (exo), 175.1 (exo), 175.8 (endo), 175.9 (endo).

Step 3: Methacrylic acid-3-(3,5-dioxo-1-phosphonooxymethyl-10-oxa-4-aza-tricyclo[5.2.1.0$^{2,6}$]dec-8-en-4-yl)-propyl ester

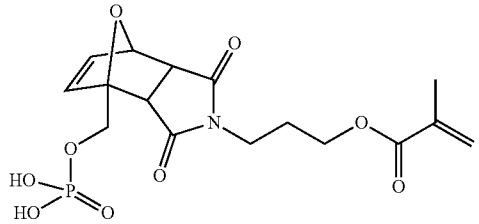 [SMILES: C=C(C)C(=O)OCCCN1C(=O)C2C3C=CC(COP(=O)(O)O)(O3)C2C1=O]

A solution of methacrylic acid-3-(1-hydroxymethyl-3,5-dioxo-10-oxa-4-aza-tricyclo[5.2.1.0$^{2,6}$]dec-8-en-4-yl)-propyl ester (3.00 g, 9.3 mmol), BHT (10 mg) and triethylamine (1.04 g, 10.3 mmol) in tetrahydrofuran (20 ml) was added dropwise to a solution of phosphoroxychloride (1.57 g, 10.3 mmol) in tetrahydrofuran (30 ml) at −5° C. After addition was complete, the suspension was stirred for 3 h at −5° C. and then water (2 ml) was added dropwise. The suspension was stirred for a further 30 min at −5° C. and the precipitate was then filtered off cold. The yellowish filtrate was washed with saturated aqueous NaCl solution (3×30 ml). The combined aqueous phases were re-extracted with tetrahydrofuran (2×30 ml). The combined organic phases were dried over Na$_2$SO$_4$, filtered and concentrated on the rotary evaporator. The brownish oil had acetonitrile (2×50 ml) added to it to remove water and was concentrated on the rotary evaporator. The residue had diethyl ether (2×50 ml) added to it and was stirred at room temperature. The solvent was decanted off after 1 h. The brown oil was dried on the rotary evaporator and under fine vacuum. 3.19 g (7.9 mmol, 85% yield, mixture of exo and endo isomer) of a hygroscopic white foam was obtained.

$^1$H-NMR (DMSO-d$_6$, 400 MHz): δ=1.65-1.75 (m, 0.4H; exo), 1.75-1.85 (m, 2H; endo), 1.87 (s, 3.6H; exo/endo), 3.02 (dd, 2H; J=28.2 Hz, 6.4 Hz; endo), 3.29 (t, 0.4H; J=7.0 Hz; exo), 3.41-3.49 (m, 2.2H; exo/endo), 3.66 (dd, 0.2H; J=7.8 Hz, 5.6 Hz; exo), 3.94-4.08 (m, 3.4H; exo/endo), 4.32 (dd, 0.2H; J=12.2 Hz, 5.2 Hz; exo), 4.42 (dd, 0.2H; J=12.2 Hz, 5.8 Hz; exo), 4.54 (q, 1H; J=6.1 Hz; endo), 5.08-5.11 (m, 1H; endo), 5.25-5.29 (m, 0.2H; exo), 5.64-5.68 (m, 1.2H; exo/endo), 6.00-6.05 (m, 1.2H; exo/endo), 6.36 (d, 0.2H; J=5.5 Hz; exo), 6.44-6.50 (m, 1.2H; exo/endo), 6.54-6.58 (m, 1H; endo), 6.66 (br s, 2.4H; exo/endo). $^{13}$C-NMR (DMSO-d$_6$, 100 MHz): δ=17.9, 26.1 (exo), 26.2 (endo), 34.6 (exo), 34.8 (endo), 45.6 (exo), 47.3 (exo), 48.0 (endo), 49.8 (endo), 61.5 (endo), 61.6 (exo), 62.9 (d, J=5 Hz; endo), 63.3 (d, J=5 Hz; exo), 78.7 (exo), 80.4 (endo), 89.7 (d, J=10 Hz; endo), 90.0 (d, J=10 Hz; exo), 125.6, 134.5 (exo), 135.4 (exo), 135.8 (endo), 136.8 (endo), 137.0 (endo), 166.4, 174.7 (exo), 174.7 (endo), 174.8 (exo), 176.1 (endo).

Example 3

Radical Photopolymerization of the Phosphoric Acid Methacrylate MATPA from Example 1

A mixture of 2.97 g of the phosphoric acid methacrylate MATPA from Example 1, 6.95 g of the cross-linker N,N'-diethyl-1,3-bis(acrylamido)-propane, 0.03 g of the photoinitiator camphorquinone and 0.05 g of the amine accelerator 4-(dimethylamino)-benzoate was prepared. A drop of the mixture was placed on a glass plate, covered with a PET film and irradiated with a Bluephase polymerization lamp (Ivoclar Vivadent AG, light intensity 1000 mW/cm$^{-2}$) for 20 s. The irradiated layer was then cured. The mixture was furthermore examined by means of photo DSC (Differential Scanning calorimetry, Perkin Elmer DSC 7) and a polymerization heat of 273 J/g was measured.

Example 4

Preparation of a Light-Curing Adhesive Based on the Phosphoric Acid Methacrylate MATPA from Example 1

An adhesive was prepared from 1.09 g of the phosphoric acid methacrylate MATPA from Example 1, 1.49 g of the monofunctional comonomer 2-hydroxyethyl methacrylate, 3.25 g of the cross-linker bis-GMA, 0.99 g of the cross-linker UDMA, 1.01 g of the cross-linker glycerol dimethacrylate, 0.02 g of the photoinitiator camphorquinone, 0.05 g of the amine accelerator 4-(dimethylamino)-benzoate, 0.10 g of the acylphosphine oxide photoinitiator Lucirin TPO and 2.00 g of the solvent ethanol. The adhesive was able to be cured by means of a Bluephase polymerization lamp (Ivoclar Vivadent AG, light intensity 1000 mW/cm$^2$).

Example 5

Synthesis of methacrylic acid-3-[3,5-dioxo-1-(11-phosphonooxyundecyloxymethyl)-10-oxa-4-aza-tricyclo[5.2.1.0$^{2,6}$]dec-8-en-4-yl]-propyl ester Step 1: 2-(11-bromoundecyloxy)-tetrahydropyran

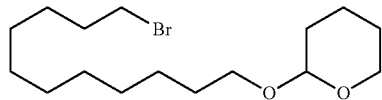 [SMILES: BrCCCCCCCCCCCOC1CCCCO1]

3,4-Dihydro-2H-pyran (21.87 g, 260 mmol) was added dropwise to a solution of 11-bromoundecanol (50.24 g, 200 mmol) and toluene-4-sulphonic acid monohydrate (80 mg, 0.4 mmol) in dichloromethane (100 ml). The reaction mixture was stirred at room temperature. After 24 h, the brown solution was filtered over a thin layer of silica gel. The filtrate was concentrated on the rotary evaporator and dried under fine vacuum. 65.85 g (196 mmol, 98% yield) of a light yellowish oil was obtained.

$^1$H-NMR (CDCl$_3$, 400 MHz): δ=1.23-1.37 (m, 12H), 1.37-1.47 (m, 2H), 1.48-1.64 (m, 6H), 1.65-1.76 (m, 1H), 1.77-1.90 (m, 3H), 3.35-3.42 (m, 3H), 3.46-3.53 (m, 1H), 3.70-3.75 (m, 1H), 3.84-3.90 (m, 1H), 4.56-4.58 (m, 1H).

$^{13}$C-NMR (CDCl$_3$, 100.6 MHz): δ=19.7, 25.4, 26.2, 28.2, 28.8, 29.4, 29.5, 29.6, 29.8, 30.8, 32.9, 33.9, 62.3, 67.7, 98.8.

Step 2: 2-[11-(Furan-2-ylmethoxy)-undecyloxy]-tetrahydropyran

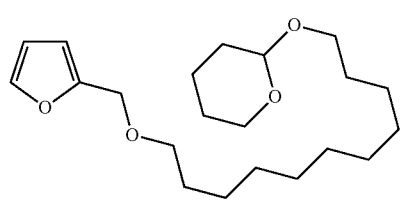 [SMILES: c1coc(COCCCCCCCCCCCOC2CCCCO2)c1]

Furfuryl alcohol (9.81 g, 100 mmol) was added dropwise to a suspension of sodium hydride (2.40 g, 100 mmol) in THF (100 ml). The suspension was stirred for 1 h at room temperature, then a solution of 2-(11-bromoundecyloxy)-tetrahydropyran (33.53 g, 100 mmol) in THF (100 ml) was added dropwise. The reaction mixture was heated for 16 h under reflux. After the cooling, quenching was carried out with saturated aqueous NH$_4$Cl solution (100 ml). The two-phase mixture was extracted with ethyl acetate (3×100 ml). The combined organic phases were dried over Na$_2$SO$_4$, filtered, concentrated on the rotary evaporator and dried under fine vacuum. The crude product was purified by means of column chromatography (SiO$_2$, dichloromethane). 20.58 g (58.4 mmol, 58% yield) of a yellowish oil was obtained.

$^1$H-NMR (CDCl$_3$, 400 MHz): δ=1.25-1.40 (m, 16H), 1.48-1.62 (m, 6H), 1.66-1.74 (m, 1H), 1.78-1.87 (m, 1H), 3.34-3.40 (m, 1H), 3.45 (t, 2H; J=6.8 Hz), 3.47-3.52 (m, 1H), 3.70-3.75 (m, 1H), 3.84-3.90 (m, 1H), 4.42 (s, 2H), 4.56-4.58 (m, 1H), 6.28-6.30 (m, 1H), 6.32-6.33 (s, 1H), 7.38-7.39 (m, 1H).

$^{13}$C-NMR (CDCl$_3$, 100.6 MHz): δ=19.7, 25.5, 26.1, 26.3, 29.1, 29.4, 29.5, 29.5, 29.5, 29.6, 29.7, 29.8, 30.8, 62.3, 64.7, 67.7, 70.4, 98.8, 108.9, 110.2, 142.6, 152.2.

Step 3: 11-(Furan-2-ylmethoxy)-undecan-1-ol

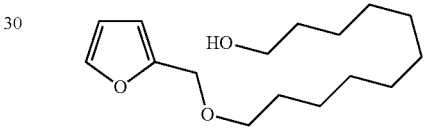

A solution of 2-[11-(furan-2-ylmethoxy)-undecyloxy]-tetrahydropyran (20.48 g, 58.1 mmol) and toluene-4-sulphonic acid monohydrate (480 mg, 2.4 mmol) in methanol (100 ml) was stirred for 20 h at room temperature. The reaction mixture was concentrated on the rotary evaporator and the crude product was purified by means of column chromatography (SiO$_2$, ethyl acetate). 7.18 g (26.8 mmol, 46% yield) of a yellowish solid was obtained.

$^1$H-NMR (CDCl$_3$, 400 MHz): δ=1.25-1.37 (m, 14H), 1.51-1.62 (m, 4H), 1.84 (s, 1H), 3.45 (t, 2H; J=6.8 Hz), 3.61 (t, 2H; J=6.8 Hz), 4.43 (s, 2H), 6.29-6.30 (m, 1H), 6.32-6.34 (m, 1H), 7.39-7.40 (m, 1H).

$^{13}$C-NMR (CDCl$_3$, 100.6 MHz): δ=25.8, 26.1, 29.4, 29.5, 29.5, 29.6, 29.6, 32.8, 62.9, 64.7, 70.4, 108.9, 110.2, 142.6, 152.1.

Step 4: Methacrylic acid-3-[3,5-dioxo-1-(11-hydroxy-undecyloxymethyl)-10-oxa-4-aza-tricyclo[5.2.1.0$^{2,6}$]dec-8-en-4-yl]-propyl ester

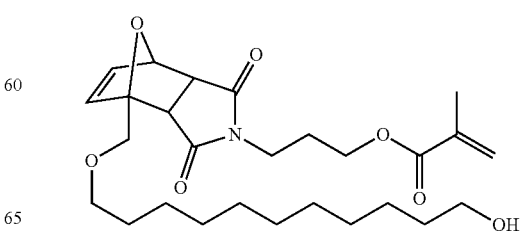

A solution of 11-(furan-2-ylmethoxy)-undecan-1-ol (7.00 g, 26.1 mmol), methacrylic acid-3-(2,5-dioxo-2,5-dihydropyrrol-1-yl)-propyl ester (5.82 g, 26.1 mmol) and BHT (10 mg) in toluene (100 ml) was heated to 80° C. accompanied by the introduction of a light air stream. After 20 h, the solution was concentrated on the rotary evaporator and the crude product was purified by means of column chromatography (SiO$_2$, ethyl acetate). 6.16 g (12.5 mmol, 48% yield, mixture of exo and endo isomer) was obtained as yellowish oil.

$^1$H-NMR (CDCl$_3$, 400 MHz): δ=1.25-1.36 (m, 22.4H; exo/endo), 1.51-1.63 (m, 6.6H; exo/endo), 1.76 (s, 1.6H; exo/endo), 1.81-1.88 (m, 1.2H; exo), 1.92-1.98 (m, 6.4H; exo/endo), 2.91 (dd, 2H; J=40.2 Hz, 6.4 Hz; endo), 3.43-3.51 (m, 2.4H; exo), 3.52-3.65 (m, 8.4H), 3.81 (d, 1H; J=11.6 Hz; endo), 4.01 (d, 0.6H; J=11.6 Hz; endo), 4.06-4.15 (m, 5H; exo/endo), 5.23-5.24 (m, 1H; endo), 5.28-5.30 (m, 0.6H; exo), 5.57-5.58 (m, 1.6H; exo/endo), 6.11-6.14 (m, 1.6H; exo/endo), 6.30-6.32 (d, 0.6H; J=5.8 Hz; exo), 6.44-6.46 (m, 0.6H; exo), 6.51-6.54 (m, 2H; endo). $^{13}$C-NMR (CDCl$_3$, 100.6 MHz): δ=18.3, 18.3, 25.7, 26.0, 26.7, 29.4, 29.4, 29.4, 29.5, 29.5, 29.5, 29.6, 32.8, 35.4, 35.7, 45.7, 47.8, 48.3, 49.9, 61.5, 61.6, 62.9, 67.9, 68.4, 72.1, 72.2, 79.6, 81.0, 90.7, 91.4, 125.6, 125.7, 135.1, 135.3, 136.1, 136.2, 136.6, 138.1, 167.2, 174.5, 174.8, 175.0, 176.0.

Step 5: Methacrylic acid-3-[3,5-dioxo-1-(11-phosphonooxyundecyloxymethyl)-10-oxa-4-aza-tricyclo[5.2.1.0$^{2,6}$]dec-8-en-4-yl]-propyl ester

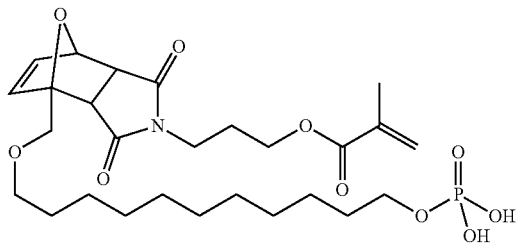 [SMILES: C=C(C)C(=O)OCCCN1C(=O)C2C3C=CC(COCCCCCCCCCCCOP(=O)(O)O)(O3)C2C1=O]

A solution of methacrylic acid-3-[3,5-dioxo-1-(11-hydroxy-undecyloxymethyl)-10-oxa-4-aza-tricyclo[5.2.1.0$^{2,6}$]dec-8-en-4-yl]-propyl ester (6.06 g, 12.3 mmol), BHT (10 mg) and triethylamine (1.37 g, 13.6 mmol) in THF (30 ml) was added dropwise at −5° C. to a solution of phosphoroxychloride (2.08 g, 13.6 mmol) in THF (50 ml). After addition was complete, the suspension was stirred for 3 h at −5° C. and then water (2 ml) was added dropwise. The suspension was stirred for a further 30 min in an ice bath and the precipitate was then filtered off cold. The yellowish filtrate was washed with saturated aqueous NaCl solution (3×50 ml). The combined aqueous phases were re-extracted with THF (2×30 ml). The combined organic phases were dried over Na$_2$SO$_4$, filtered and concentrated on the rotary evaporator. The brownish oil had acetonitrile (2×50 ml) added to it to remove water and was concentrated on the rotary evaporator. The brown oil had diethyl ether (4×100 ml) added to it and was stirred at room temperature for 10 min. A dark-brown oil precipitated out. The solvent was decanted off. The combined ether solution was concentrated on the rotary evaporator and dried under fine vacuum. 3.87 g (6.8 mmol, 55% yield, mixture of exo and endo isomer) of a brownish oil was obtained.

$^1$H-NMR (DMSO-d$_6$, 400 MHz): δ=1.22-1.32 (m, 22.4H; exo/endo), 1.43-1.60 (m, 6.6H; exo/endo), 1.69-1.76 (m, 1.2H; exo), 1.80-1.85 (m, 2H; endo), 1.87-1.91 (m, 5.8H; exo/endo), 2.96 (dd, 2H; J=55.6 Hz, 6.4 Hz; endo), 3.30 (t, 1H; J=6.4 Hz; endo), 3.36-3.54 (m, 6H; endo), 3.59-3.66 (m, 1.6H; exo/endo), 3.90-4.09 (m, 7.2H; exo/endo), 5.08-5.09 (m, 1H; endo), 5.24-5.26 (m, 0.6H; exo), 5.67-5.69 (m, 1.6H; exo/endo), 6.00-6.06 (m, 1.6H; exo/endo), 6.32-6.34 (m, 0.6H; exo), 6.43-6.47 (m, 1.6H; exo/endo), 6.52-6.55 (m, 1H; endo), 8.68 (br s, 3.2H; exo/endo).

$^{13}$C-NMR (DMSO-d$_6$, 100.6 MHz): δ=17.9, 25.1, 25.5, 26.1, 28.6, 28.8, 29.0, 29.0, 29.0, 29.8, 29.9, 30.4, 34.7, 45.5, 47.3, 48.1, 49.6, 61.3, 61.6, 65.2 (d; J=5 Hz), 67.6, 68.1, 70.9, 71.0, 78.7, 80.3, 90.3, 90.8, 125.6, 134.5, 135.9, 135.8, 136.4, 137.6, 166.3, 166.4, 174.7, 174.9, 175.0, 176.2.

$^{31}$P-NMR (DMSO-d$_6$, 162 MHz): δ=−1.1.

Example 6

Synthesis of methacrylic acid-3,5-dioxo-4-(10-phosphonooxy-decyl)-10-oxa-4-aza-tricyclo[5.2.1.0$^{2,6}$]dec-8-en-1-ylmethyl ester Step 1: 4-(10-Hydroxy-decyl)-10-oxa-4-aza-tricyclo[5.2.1.0$^{2,6}$]dec-8-ene-3,5-dione

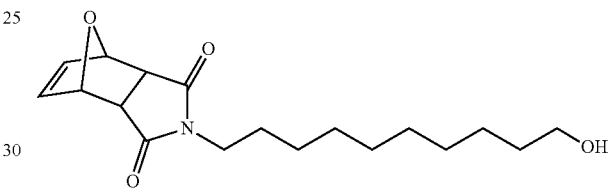

A solution of 10-amino-1-decanol (5.36 g, 30.9 mmol) in methanol (20 ml) was added dropwise to a suspension of 4,10-dioxatricyclo[5.2.1.0$^{2,6}$]dec-8-ene-3,5-dione (5.13 g, 30.9 mmol) in methanol (30 ml). The reaction mixture was heated under reflux for 24 h and then concentrated on the rotary evaporator. The crude product was purified by means of column chromatography (SiO$_2$, ethyl acetate). 1.52 g (4.7 mmol, 15% yield) of a yellowish solid was obtained.

$^1$H-NMR (CDCl$_3$, 400 MHz): δ=1.22-1.37 (m, 12H), 1.51-1.59 (m, 4H), 2.60 (br s, 1H), 2.84 (s, 2H), 3.46 (t, 2H; J=7.4 Hz), 3.62 (t, 2H; J=6.5 Hz), 5.26 (s, 2H), 6.51 (s, 2H).

$^{13}$C-NMR (CDCl$_3$, 100.6 MHz): δ=25.7, 26.6, 27.5, 29.0, 29.3, 29.3, 29.4, 32.7, 39.0, 47.4, 62.9, 80.9, 136.6, 176.4.

Step 2: 1-(10-Hydroxy-decyl)-pyrrole-2,5-dione

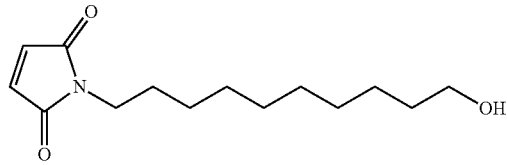 [SMILES: O=C1C=CC(=O)N1CCCCCCCCCCO]

A suspension of 4-(10-hydroxy-decyl)-10-oxa-4-aza-tricyclo[5.2.1.0$^{2,6}$]-dec-8-ene-3,5-dione (1.52 g, 4.7 mmol) in toluene (50 ml) was heated under reflux for 16 h. The solution was decanted off from the undissolved residue, concentrated on the rotary evaporator and dried under fine vacuum. 1.15 g (4.5 mmol, 97% yield) of a white solid was obtained.

$^1$H-NMR (CDCl$_3$, 400 MHz): δ=1.25-1.36 (m, 12H), 1.52-1.61 (m, 4H), 2.63 (br s, 1H), 3.50 (t, 2H; J=7.2 Hz), 3.63 (t, 2H; J=6.8 Hz), 6.69 (s, 2H).

$^{13}$C-NMR (CDCl$_3$, 100.6 MHz): δ=25.7, 26.7, 28.5, 29.0, 29.3, 29.4, 32.7, 37.9, 63.0, 134.0, 170.9.

Step 3: Methacrylic acid-4-(10-hydroxydecyl)-3,5-dioxo-10-oxa-4-aza-tricyclo[5.2.1.0$^{2,6}$]dec-8-en-1-ylmethyl ester

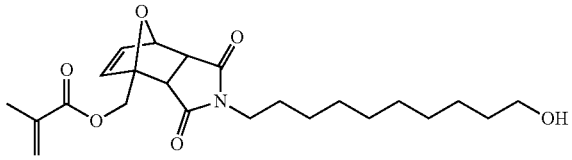 [SMILES: C=C(C)C(=O)OCC12C=CC(O1)C1C(=O)N(CCCCCCCCCCO)C(=O)C12]

A solution of furfuryl methacrylate (750 mg, 4.5 mmol), 1-(10-hydroxy-decyl)-pyrrole-2,5-dione (1.05 g, 4.1 mmol) and BHT (5 mg) in toluene (30 ml) was heated to 80° C. accompanied by the introduction of a light air stream. After 20 h the reaction solution was concentrated on the rotary evaporator and dried under fine vacuum. The crude product was purified by column chromatography (SiO$_2$, n-hexane/ethyl acetate 1:1). 560 mg (1.3 mmol, 33% yield) of the endo isomer was obtained as a white solid and 430 mg (1.0 mmol, 25% yield) of the exo isomer as a yellowish oil.
Endo Isomer:
$^1$H-NMR (CDCl$_3$, 400 MHz): δ=1.19-1.36 (m, 12H), 1.37-1.46 (m, 2H), 1.52-1.61 (m, 3H), 1.97 (s, 3H), 3.31 (t, 2H; J=7.6 Hz), 3.38 (d, 1H; J=7.6 Hz), 3.61-3.66 (m, 3H), 4.69 (d, 1H; J=12.8 Hz), 4.91 (d, 1H; J=12.8 Hz), 5.31 (dd, 1H; J=5.3 Hz, 1.7 Hz), 5.61-5.61 (m, 1H), 6.17 (s, 1H), 6.36 (d, 1H; J=5.8 Hz), 6.45 (dd, 1H; J=5.7 Hz, 1.6 Hz).
$^{13}$C-NMR (CDCl$_3$, 100.6 MHz): δ=18.3, 25.7, 26.8, 27.4, 29.0, 29.3, 29.4, 32.8, 38.7, 46.8, 47.7, 62.2, 62.9, 79.6, 89.8, 126.5, 134.4, 135.6, 135.7, 166.8, 174.4, 174.6.
Exo Isomer:
$^1$H-NMR (CDCl$_3$, 400 MHz): δ=1.25-1.35 (m, 12H), 1.52-1.58 (m, 4H), 1.95 (s, 3H), 1.99 (br s, 1H), 2.95 (dd, 2H; J=28.2 Hz, 6.5 Hz), 3.46 (t, 2H; J=7.5 Hz), 3.61 (t, 2H; J=6.8 Hz), 4.52 (d, 1H; J=12.8 Hz), 4.98 (d, 1H; J=12.8 Hz), 5.27 (d, 1H; J=1.6 Hz), 5.59-5.61 (m, 1H), 6.13 (s, 1H), 6.45 (d, 1H; J=5.8 Hz), 6.56 (dd, 1H; J=5.6 Hz, 1.6 Hz).
$^{13}$C-NMR (CDCl$_3$, 100.6 MHz): δ=18.3, 25.8, 26.6, 27.5, 29.0, 29.3, 29.3, 29.4, 32.8, 39.0, 48.3, 49.9, 61.6, 62.9, 81.1, 89.6, 126.3, 135.8, 137.1, 137.4, 166.8, 174.3, 175.8.

Step 4: Methacrylic acid-3,5-dioxo-4-(10-phosphonooxy-decyl)-10-oxa-4-aza-tricyclo[5.2.1.0$^{2,6}$]dec-8-en-1-ylmethyl ester A solution of endo/exo methacrylic acid-4-(10-hydroxydecyl)-3,5-dioxo-10-oxa-4-aza-tricyclo[5.2.1.0$^{2,6}$]dec-8-en-1-ylmethyl ester (890 mg, 2.1 mmol), BHT (5 mg) and triethylamine (240 mg, 2.3 mmol) in THF (30 ml) was added dropwise to a solution of phosphoroxychloride (360 mg, 2.3 mmol) in THF (20 ml) at −5° C. After addition was complete, the suspension was stirred for 3 h at −5° C. and then water (2 ml) was added dropwise. The suspension was stirred for a further 30 min in the ice bath and the precipitate was then filtered off cold. The yellowish filtrate was washed with saturated aqueous NaCl solution (3×50 ml). The combined aqueous phases were re-extracted with THF (2×30 ml). The combined organic phases were dried over Na$_2$SO$_4$, filtered and concentrated on the rotary evaporator. The brownish oil had acetonitrile (2×50 ml) added to it to remove water and was concentrated on the rotary evaporator. The residue was dried under fine vacuum. 1.01 g (2.0 mmol, 95% yield, mixture of exo and endo isomer) of a colourless oil was obtained.

Example 7

Preparation of DoD Adhesives Based on the Methacrylate Phosphates from Examples 5 and 6

3 primer solutions were prepared in order to examine the shear adhesion between a ZrO$_2$ ceramic and a composite cement according to the invention. These were solutions of 1 wt.-% each of the methacrylate phosphate from Example 5 (primer A), of the methacrylate phosphate from Example 6 (primer B) and of 10-methacryloyloxydecyl phosphate (primer C, comparison) in ethanol respectively.

To determine the bond strength the respective primer solutions were applied to ZrO$_2$ ceramic testpieces (IPS e.max ZirCAD, Ivoclar Vivadent, yttrium-stabilized zirconium oxide) and the solvent was blown off. The composite cement Multilink Automix (Ivoclar Vivadent) was then applied to the primer layer and cured for 20 s with the Bluephase C8 LED lamp (Ivoclar Vivadent) and then for 3 min in the Spectramat light furnace (Ivoclar Vivadent). The testpieces were then stored in water for 24 h at 37° C. and the adhesive shear strength was measured analogously to the ISO guideline "ISO 1994-ISO TR 11405: Dental Materials Guidance on Testing of Adhesion to Tooth Structure". In a second run, the testpieces were additionally stored in a drying oven at 130° C. for 60 min after water storage and only then was the shear adhesion determined after rapid cooling of the testpieces. The results are presented in Tab. 1 and show that with a temperature load of the ceramic composite bond the primers with the adhesive monomers according to the invention display a much greater decrease in the bond strength and therefore such a bond can be more easily debonded.

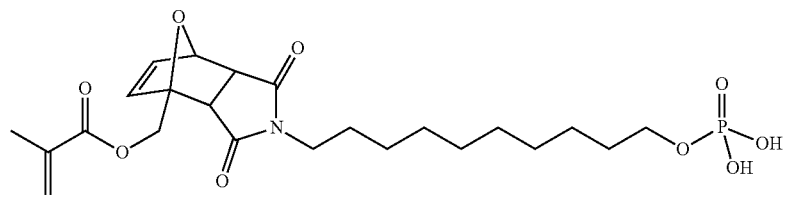 [SMILES: C=C(C)C(=O)OCC12C=CC(O1)C1C(=O)N(CCCCCCCCCCOP(=O)(O)O)C(=O)C12]

TABLE 1

Adhesive shear strength (ASS, in MPa) of the bond between ZrO$_2$ ceramic and composite cement

| Primer | ASS after WS[a] | ASS after WS + TT[b] |
|---|---|---|
| A | 28.4 | 13.9 |
| B | 21.6 | 10.3 |
| C (comparison) | 30.1 | 21.7 |

[a]WS = water storage, [b]WS + TT = water storage and thermal treatment

Example 8

Synthesis of 4-[4(5)-(methacryloyloxymethyl)-2-pyridin-2-yl-3,6-dihydro-2H-thiopyran-2-ylsulphanylmethyl]-benzoic acid-2-(methacryloyloxy)-ethyl ester

Step 1: 2-Benzenesulphonylmethylpyridine

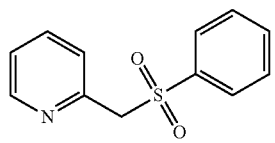 [SMILES: O=S(=O)(Cc1ccccn1)c1ccccc1]

A suspension of 2-(chloromethyl)pyridine hydrochloride (32.81 g, 200 mmol) in acetonitrile (200 ml) had sodium phenyl sulphinate (49.24 g, 300 mmol), tetrapropylammonium bromide (10.64 g, 40 mmol) and 1,8-diazabicyclo[5.4.0]undec-7-ene (30.44 g, 200 mmol) added to it. The reaction mixture was heated under reflux for 16 h and then concentrated on the rotary evaporator. The residue was taken up in dichloromethane (200 ml), washed with saturated aqueous NaCl solution (3×100 ml), dried over Na$_2$SO$_4$, filtered and concentrated to approximately half the volume on the rotary evaporator. The brown solution was filtered over a layer of silica gel. 41.55 g (178 mmol; 89% yield) of a yellowish solid was obtained.

$^1$H-NMR (CDCl$_3$, 400 MHz): δ=4.56 (s, 2H), 7.21-7.24 (m, 1H), 7.42-7.48 (m, 3H), 7.58-7.62 (m, 1H), 7.66-7.70 (m, 3H), 8.41-8.42 (m, 1H).

$^{13}$C-NMR (CDCl$_3$, 100.6 MHz): δ=64.6, 123.4, 125.7, 128.4, 129.0, 133.8, 136.7, 138.2, 148.8, 149.7.

Step 2: 4-(Pyridine-2-carbothioylsulphanylmethyl)-benzoic acid

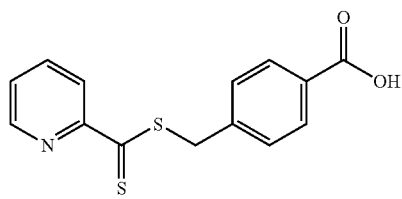 [SMILES: O=C(O)c1ccc(CSC(=S)c2ccccn2)cc1]

A solution of 1,8-diazabicyclo[5.4.0]undec-7-ene (79.56 g, 523 mmol) in acetonitrile (100 ml) was added dropwise to a suspension of 2-benzenesulphonylmethylpyridine (40.64 g, 174 mmol) and sulphur (16.76 g, 523 mmol) in acetonitrile (500 ml) accompanied by ice cooling. After addition was complete, the dark red solution was stirred for 22 h at room temperature. 4-(Bromomethyl)benzoic acid (37.46 g, 174 mmol) was then added in portions. The reaction mixture was stirred for a further 4 h at room temperature and then had 2N hydrochloric acid (200 ml) added to it (pH=1). A red precipitate precipitated out of the red solution. The suspension was filtered and the filtration residue was washed with acetonitrile (100 ml). The filtrate had tert-butyl methyl ether (200 ml) and saturated aqueous NaCl solution (100 ml) added to it. The phases were separated and the organic phase was washed with saturated aqueous NaCl solution (2×100 ml). The combined aqueous phases were then re-extracted with tert-butyl methyl ether (100 ml). The combined organic phases were dried over Na$_2$SO$_4$, filtered and concentrated on the rotary evaporator. The residue was combined with the previously obtained filtration residue, had acetonitrile (200 ml) added to it and was stirred for 4 h at room temperature. The obtained suspension was then filtered. The filtration residue was washed with acetonitrile (50 ml) and dried in the vacuum drying oven (50° C., 125 mbar). 44.95 g (155 mmol; 89% yield) of a red solid was obtained.

$^1$H-NMR (DMSO-d$_6$, 400 MHz): δ=4.66 (s, 2H), 7.56-7.58 (m, 2H), 7.70-7.73 (m, 1H), 7.94-7.96 (m, 2H), 7.00-8.03 (m, 1H), 8.26-8.28 (m, 1H), 8.66-8.68 (m, 1H), 13.03 (s, 1H). $^{13}$C-NMR (DMSO-d$_6$, 100.6 MHz): δ=39.6, 121.9, 127.8, 129.4, 129.5, 129.9, 137.7, 140.6, 148.3, 155.3, 166.9, 226.0.

Step 3: 4-(Pyridine-2-carbothioylsulphanylmethyl)-benzoic acid-2-(methacryloyloxy)-ethyl ester

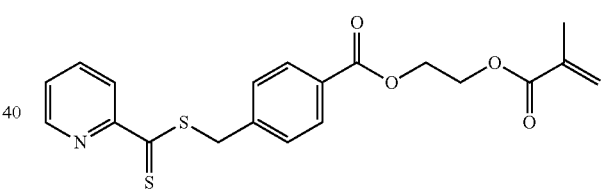

A suspension of 4-(pyridine-2-carbothioylsulphanylmethyl)-benzoic acid (10.39 g, 35.9 mmol), 2-hydroxyethyl methacrylate (4.67 g, 35.9 mmol), N,N-dimethylaminopyridine (600 mg, 5.0 mmol) and BHT (10 mg) in dichloromethane (100 ml) was cooled to 0° C. 3-(Ethyliminomethylideneamino)-N,N-dimethyl-propane-1-aminehydrochloride (8.26 g, 43.1 mmol) was added and the reaction mixture was stirred for 1 h at 0° C. and for 16 h at room temperature. The red reaction solution was filtered over a layer of silica gel (SiO$_2$, dichloromethane) and the filtrate was concentrated on the rotary evaporator. The oily red solid had n-hexane (100 ml) added to it, was stirred for 20 h at room temperature and filtered. The filtration residue was washed with n-hexane (50 ml) and dried in the vacuum drying oven (50° C., 125 mbar). 11.22 g (27.9 mmol; 78% yield) of a light red solid was obtained.

$^1$H-NMR (CDCl$_3$, 400 MHz): δ=1.95 (s, 3H), 4.47-4.50 (m, 2H), 4.54-4.58 (m, 4H), 5.58-5.59 (m, 1H), 6.13-6.14 (m, 1H), 7.46-7.49 (m, 3H), 7.7-7.81 (m, 1H), 7.98-8.00 (m, 2H), 8.31-8.33 (m, 1H), 8.59-8.61 (m, 1H).

$^{13}$C-NMR (CDCl$_3$, 100.6 MHz): δ=18.3, 40.8, 62.4, 62.7, 122.3, 126.2, 127.0, 129.0, 129.5, 130.0, 135.9, 137.0, 141.0, 148.0, 156.1, 166.0, 167.1, 225.4.

Step 4: Methacrylic acid-2-methylene-but-3-enyl ester

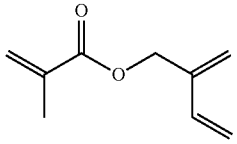

Lithium diisopropylamide (30 wt.-% in paraffin oil, 53.58 g, 150 mol) had diethyl ether (150 ml) added to it and was cooled to −5° C. Isoprene monoxide (11.78 g, 140 mmol) was then added dropwise. The reaction mixture was stirred for 3 h at −5° C. and then for 1 h at room temperature. Accompanied by ice cooling, 2N hydrochloric acid (100 ml) was added and the phases were separated. The organic phase was washed with aqueous NaHCO₃ solution (5 wt.-%; 100 ml) and the combined aqueous phases were re-extracted with diethyl ether (5×50 ml). The combined organic phases were then dried over Na₂SO₄, filtered and concentrated on the rotary evaporator (40° C., 750 mbar–90 mbar). The obtained yellowish oil was extracted with acetonitrile (3×100 ml) and the combined acetonitrile solutions were concentrated on the rotary evaporator (40° C., 150 mbar–90 mbar). The thus-obtained yellow liquid was dissolved in dichloromethane (70 ml). Triethylamine (5.06 g, 50.0 mmol) and N,N-dimethylaminopyridine (600 mg, 5.0 mmol) were added and the solution was cooled to −5° C. A solution of methacrylic anhydride (7.71 g, 50.0 mmol) and BHT (10 mg) in dichloromethane (30 ml) was added dropwise. The reaction mixture was stirred for 2 h at −5° C. and for 22 h at room temperature, washed with water (3×100 ml), dried over Na₂SO₄, filtered and concentrated on the rotary evaporator. The yellow-brown oil was dissolved in dichloromethane (50 ml) and filtered over a layer of silica gel. The filtrate was concentrated on the rotary evaporator and dried under fine vacuum. 3.85 g (25.3 mmol; 51% yield) of a yellow liquid was obtained.

$^1$H-NMR (CDCl₃, 400 MHz): δ=1.97 (s, 3H), 4.84 (s, 2H), 5.14 (d, J=11.2 Hz; 1H), 5.22-5.29 (m, 3H), 5.58 (s, 1H), 6.14 (s, 1H), 6.39 (dd, J=11.0 Hz, 17.8 Hz; 1H).

$^{13}$C-NMR (CDCl₃, 100.6 MHz): δ=18.3, 63.7, 114.6, 117.8, 125.7, 136.2, 136.2, 140.7, 167.0.

Step 5: 4-[4(5)-(Methacryloyloxymethyl)-2-pyridin-2-yl-3,6-dihydro-2H-thiopyran-2-ylsulphanylmethyl]-benzoic acid-2-(methacryloyloxy)-ethyl ester

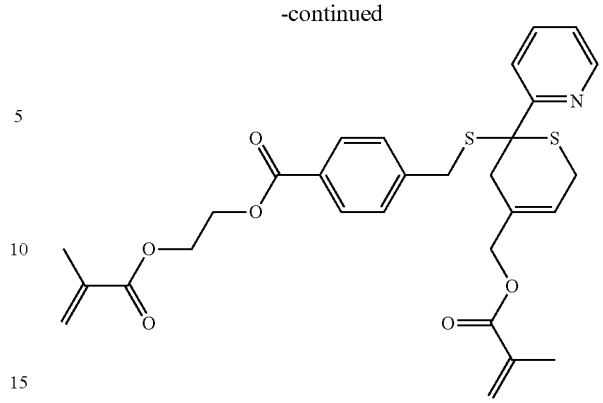

4-(Pyridine-2-carbothioylsulphanylmethyl)-benzoic acid-2-(methacryl-oyloxy)-ethyl ester (6.59 g, 16.4 mmol) and trifluoroacetic acid (1.87 g, 16.4 mmol) were dissolved in chloroform (70 ml). A solution of methacrylic acid-2-methylene-but-3-enyl ester (3.75 g, 24.6 mmol) in chloroform (30 ml) was added dropwise. The initially red solution was stirred for 24 h at room temperature, wherein an increasing decolourization occurred. The solution was then washed with aqueous NaHCO₃ solution (5 wt.-%; 3×50 ml), dried over Na₂SO₄, filtered and concentrated on the rotary evaporator. The slightly reddish crude product was purified by column chromatography (SiO₂, n-hexane/ethyl acetate 4:1). 7.22 g (13.0 mmol; 80% yield) of the inseparable isomer mixture was obtained as a yellowish oil.

$^1$H-NMR (CDCl₃, 400 MHz): δ=1.94 (s, 3H), 1.95 (s, 3H), 2.84-2.95 (m, 1H), 3.07-3.20 (m, 2H), 3.44-3.56 (m, 2H), 3.78 (d, J=12.8 Hz; 1H), 4.46-4.48 (m, 2H), 4.53-4.55 (m, 2H), 4.57-4.63 (m, 2H), 5.56-5.59 (m, 2H), 5.88-5.89 (m, 0.7H), 5.97-5.98 (m, 0.3H), 6.12 (s, 1H), 6.13 (s, 1H), 7.13-7.16 (m, 3H), 7.60-7.65 (m, 1H), 7.69-7.74 (m, 1H), 7.82-7.85 (m, 2H), 8.51-8.54 (m, 1H). $^{13}$C-NMR (CDCl₃, 100.6 MHz): δ=18.3, 18.3, 26.1, 26.4, 35.1, 38.9, 39.4, 61.1, 62.4, 62.6, 68.1, 68.7, 121.5, 121.6, 122.5, 122.6, 124.9, 125.8, 126.1, 128.2, 128.2, 129.0, 129.0, 129.6, 129.7, 129.8, 132.2, 135.9, 136.1, 136.7, 136.7, 143.2, 143.4, 148.1, 148.2, 161.2, 161.4, 166.0, 167.0, 167.1.

Example 9

Synthesis of methacrylic acid-4-[3-(methacryloyloxy)-propyl]-3,5-dioxo-10-oxa-4-aza-tricyclo[5.2.1.0$^{2,6}$]dec-8-en-1-ylmethyl ester

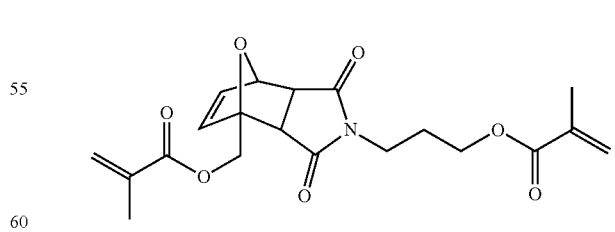

1-Hydroxymethyl-4-(3-hydroxy-propyl)-10-oxa-4-aza-tricyclo[5.2.1.0$^{2,6}$]dec-8-ene-3,5-dione (18.29 g, 72.2 mmol), triethylamine (16.08 g, 159 mmol), N,N-dimethylaminopyridine (600 mg, 5.0 mmol) and BHT (10 mg) were dissolved in dichloromethane (100 ml). A solution of methacrylic anhydride (24.49 g, 159 mmol) in dichloromethane (50 ml) was added dropwise at 0° C. The clear yellow solution was stirred for 2 h at −0° C., then the ice bath was removed and stirring was continued at room temperature. After 22 h the reaction solution was washed with water (3×100 ml). The combined aqueous phases were re-extracted with dichloromethane (100 ml). The combined organic phases were dried over Na₂SO₄, filtered and concentrated on the rotary evaporator. The brownish oil was purified by means of column chromatography (SiO₂, n-hexane/ethyl acetate 2:1). 15.04 g (38.6 mmol, 53% yield, mixture of exo and endo isomer) of a yellow oil was obtained.

¹H-NMR (DMSO-d₆, 400 MHz): δ=1.81-1.90 (m, 9.6H; exo/endo), 3.04 (d, 1H; J=6.5 Hz; endo), 3.10 (d, 1H; J=6.5 Hz; endo), 3.31-3.35 (m, 0.4H; exo), 3.47-3.51 (m, 2.2H; exo/endo), 3.70-3.73 (m, 0.2H; exo), 3.99-4.05 (m, 2.4H; exo/endo), 4.41 (d, 1H; J=12.6 Hz; endo), 4.63 (d, 0.2H; J=12.8 Hz; exo), 4.79 (d, 0.2H; J=12.8 Hz; exo), 4.84 (d, 1H; J=12.6 Hz; endo), 5.15 (d, 1H; J=1.6 Hz; endo), 5.32 (dd, 0.2H; J=5.6 Hz, 1.5 Hz; exo), 5.67-5.69 (m, 2.2H; exo/endo), 5.71-5.73 (m, 0.2H; exo), 6.01-6.08 (m, 2.4H; exo/endo), 6.42 (d, 0.2H; J=6.1 Hz; exo), 6.49-6.53 (m, 1.2H; exo/endo), 6.60-6.62 (m, 1H; endo).

¹³C-NMR (DMSO-d₆, 100.6 MHz): δ=17.8 (endo), (17.8; exo), 17.9, (26.2), 26.2, (34.6), 34.9, (46.4), (47.3), 48.2, 49.7, 61.4, (61.5), 61.6, (62.0), (78.8), 80.5, 88.8 (89.1), 125.5, 126.1, (126.3), (134.3), (135.4), 135.5, (135.7), 135.8, 136.6, 137.2, 166.0, 166.4, (174.5), (174.6), 174.7, 176.0.

Example 10

Synthesis of methacrylic acid-3,5-dioxo-4-(3-triethoxysilylpropyl)-10-oxa-4-aza-tricyclo[5.2.1.0²,⁶]dec-8-en-1-ylmethyl ester Step 1: N-(3-Triethoxysilylpropyl)-maleimide (SI126)

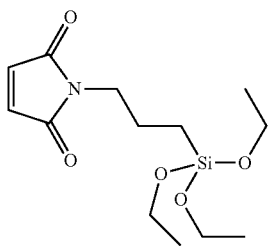 [SMILES: CCO[Si](CCCN1C(=O)C=CC1=O)(OCC)OCC]

Maleic anhydride (29.42 g, 300 mmol) was suspended in toluene (100 ml). A solution of 3-aminopropyltriethoxysilane (66.41 g, 300 mmol) in toluene (75 ml) was added dropwise and the reaction solution was stirred at room temperature. After 2 h zinc chloride (13.63 g, 100 mmol) was added first, then a solution of hexamethyldisilazane (60.52 g, 375 mmol) in toluene (75 ml) was added dropwise. The suspension was heated under reflux for 24 h and filtered over Celatom after cooling to room temperature. The filtrate was concentrated on the rotary evaporator and dried under fine vacuum. The crude product was purified by vacuum distillation (bp: 125° C./0.03 mbar). 15.14 g (50.3 mmol, 17% yield) of a colourless liquid was obtained.

¹H-NMR (CDCl₃, 400 MHz): δ=0.41-0.49 (m, 2H), 1.08 (t, 9H; J=7.1 Hz), 1.49-1.60 (m, 2H), 3.37 (t, 2H; J=7.3 Hz), 3.60-3.70 (m, 6H), 6.59 (s, 2H).

¹³C-NMR (CDCl₃, 100.6 MHz): δ=6.1, 16.7, 20.5, 38.7, 56.8, 132.5, 169.2.

²⁹Si-NMR (CDCl₃, 79.5 MHz): δ=−46.4.

Step 2: Methacrylic acid-3,5-dioxo-4-(3-triethoxysilylpropyl)-10-oxa-4-aza-tricyclo[5.2.1.0²,⁶]dec-8-en-1-ylmethyl ester

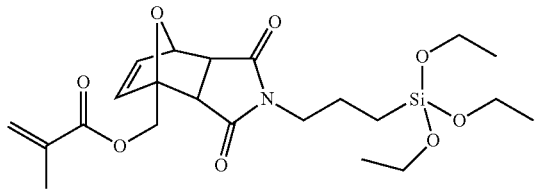 [SMILES: C=C(C)C(=O)OCC12C=CC(O1)C1C(=O)N(CCC[Si](OCC)(OCC)OCC)C(=O)C12]

A solution of furfuryl methacrylate (8.24 g, 49.6 mmol), N-(3-triethoxysilylpropyl)-maleimide (14.94 g, 49.6 mmol) and BHT (10 mg) in toluene (150 ml) was heated to 80° C. accompanied by the introduction of a light air stream. After 20 h the solvent was concentrated on the rotary evaporator and the crude product was purified by means of column chromatography (SiO₂, n-hexane/ethyl acetate 2:1). 5.67 g (12.1 mmol, 24% yield, mixture of exo and endo isomer) of a colourless oil was obtained.

¹H-NMR (CDCl₃, 400 MHz): δ=0.43-0.47 (m, 2.2H; exo/endo), 1.06-1.10 (m, 9.9H; exo/endo), 1.37-1.46 (m, 0.2H; exo), 1.50-1.58 (m, 2H, endo), 1.82 (s, 3H; endo), 1.84 (s, 0.3H; exo), 2.85 (dd, 2H, J=28.2 Hz, 6.4 Hz; endo), 3.19 (t, 0.2H; J=7.3 Hz; exo), 3.28 (d, 0.2H; J=7.3 Hz; exo), 3.35 (t, 2H; J=7.3 Hz; endo), 3.63-3.71 (m, 6.6H; exo/endo), 4.38 (d, 1H, J=12.7 Hz; endo), 4.56 (d, 0.1H, J=12.7 Hz; exo), 4.78 (d, 0.1H, J=12.7 Hz; exo), 4.87 (d, 1H, J=12.7 Hz; endo), 5.15 (s, 1H; endo), 5.18-5.20 (m, 0.1H; exo), 5.48 (s, 1H; endo), 5.50 (s, 0.1H; exo), 6.00 (s, 1H; endo), 6.05 (s, 0.1H; exo), 6.22 (d, 0.1H, J=5.4 Hz; exo), 6.34 (d, 1.1H, J=5.4 Hz; endo/exo), 6.45-6.47 (m, 1H; endo).

¹³C-NMR (CDCl₃, 100.6 MHz): δ=5.9 (endo), 6.3 (exo), 16.6, 19.5, 45.2 (exo), 46.1 (exo), 46.7 (endo), 48.3 (endo), 56.7, 60.0 (endo), 60.6 (exo), 77.9 (exo), 79.4 (endo), 87.9 (endo), 78.1 (exo), 124.6 (endo), 124.8 (exo), 132.8 (exo), 134.0 (exo), 134.1 (exo), 134.1 (endo), 135.5 (endo), 135.8 (endo), 165.1, 172.7 (endo), 172.8 (exo), 172.9 (exo), 174.2 (endo).

²⁹Si-NMR (CDCl₃, 79.5 MHz): δ=−46.6 (exo), −46.3 (endo).

Example 11

Synthesis of bis-(4-methacryloyloxybenzoyl)-diethylgermanium

Step 1: 2-(4-Methoxyphenyl)-1,3-dithiane

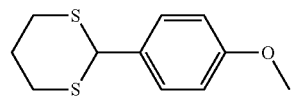

A solution of p-anisaldehyde (136.2 g, 1.0 mol) in chloroform (500 ml) had 1,3-propanedithiol (108.2 g, 1.0 mol) added to it and was cooled to −10° C. An HCl gas stream was passed through the suspension for 45 min. Stirring was then carried out for a further 30 min at 0° C., then the cooling bath was removed and the reaction mixture was stirred for 16 h at room temperature. The solvent was removed on the rotary evaporator and the residue had methanol (300 ml) added to it. The suspension was stirred for 24 h at room temperature and filtered. The filtration residue was washed with methanol (50 ml) and dried in the vacuum drying oven (125 mbar, 50° C.). 219.9 g (970 mmol, 97% yield) of a white solid was obtained (mp: 117-119° C.)

$^1$H-NMR (CDCl$_3$, 400 MHz): δ=1.87-1.97 (m, 1H, —CH$_2$—), 2.13-2.20 (m, 1H, —CH$_2$—), 2.88-2.93 (m, 2H, S—CH$_2$—), 3.02-3.09 (m, 2H, S—CH$_2$—), 3.79 (s, 3H, O—CH$_3$), 5.13 (s, 1H, S—CH—S), 6.85-6.87 (m, 2H, Ar—H$^{3,5}$), 7.38-7.40 (m, 2H, Ar—H$^{2,6}$).

$^{13}$C-NMR (CDCl$_3$, 100.6 MHz): δ=25.1 (—CH$_2$—), 32.2 (—CH$_2$—), 50.1 (S—C—S), 55.3 (O—CH$_3$), 114.1 (Ar—C$^{3,5}$), 128.9 (Ar—C$^{2,6}$), 131.3 (Ar—C$^1$), 159.6 (Ar—C$^4$).

Step 2: Bis-[2-(4-methoxyphenyl)-1,3-dithian-2-yl]-diethylgermanium

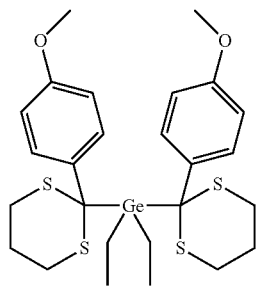

2-(4-Methoxyphenyl)-1,3-dithiane (113.2 g, 500 mmol) was dissolved in absolute THF (500 ml) under protective gas and cooled to −5° C. A 2.5 M butyllithium solution in n-hexane (200 ml, 500 mmol) was added dropwise. The brown reaction solution was then stirred for 3 h at −5° C., then a solution of diethylgermanium dichloride (42.0 g, 208 mmol) in absolute THF (100 ml) was added dropwise. The reaction mixture was stirred further overnight in the thawing ice bath, then water (200 ml) and ethyl acetate (400 ml) were added and the phases were separated. The organic phase was washed with water (2×125 ml) and the combined aqueous phases were re-extracted with ethyl acetate (150 ml). The combined organic phases were washed with saturated aqueous NaCl solution (150 ml), dried over Na$_2$SO$_4$, filtered, concentrated on the rotary evaporator and dried under fine vacuum. The residue had ethyl acetate (100 ml) added to it and the suspension was stirred at room temperature. After 20 h methanol (100 ml) was added and after a further 24 h the suspension was filtered. The filtration residue was washed with ethyl acetate (20 ml) and dried in the vacuum drying oven (125 mbar, 50° C.). 88.8 g (153 mol, 73% yield) of a white solid was obtained (mp: 115-116° C.)

$^1$H-NMR (CDCl$_3$, 400 MHz): δ=1.15 (m, 6H, —CH$_3$), 1.28 (m, 4H, Ge—CH$_2$—), 1.77-1.81 (m, 2H, —CH$_2$—), 1.94-2.05 (m, 2H, —CH$_2$—), 2.24-2.29 (m, 4H, S—CH$_2$—), 2.70-2.77 (m, 4H, S—CH$_2$—), 3.82 (s, 6H, O—CH$_3$), 6.80-6.82 (m, 4H, Ar—H$^{3,5}$), 7.78-7.80 (m, 4H, Ar—H$^{2,6}$).

$^{13}$C-NMR (CDCl$_3$, 100.6 MHz): δ=4.5 (—CH$_3$), 10.2 (Ge—CH$_2$—), 25.2 (—CH$_2$—), 25.6 (S—CH$_2$—), 51.2 (Ge—C—S), 55.2 (O—CH$_3$), 113.3 (Ar—C$^{3,5}$), 131.4 (Ar—C$^{2,6}$), 132.5 (Ar—C$^1$), 157.5 (Ar—C$^4$).

Step 3: Bis-(4-methoxybenzoyl)-diethylgermanium

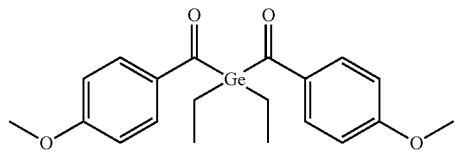

A solution of bis-[2-(4-methoxyphenyl)-1,3-dithian-2-yl]-diethylgermanium (87.21 g, 150 mol) in THF (900 ml) had water (220 ml) added to it. Calcium carbonate (180.2 g, 1.80 mol) and iodine (456.9 g, 1.80 mol) were divided into eight identical portions each. After intervals of 30 min in each case, one portion each of CaCO$_3$ and iodine was added to the reaction mixture accompanied by intermittent ice-cooling. After addition was complete, the reaction mixture was stirred for 24 h at room temperature and then filtered over a thin layer of silica gel. The red-brown filtrate had saturated aqueous sodium dithionite solution (1600 ml) added to it accompanied by intensive stirring, until the colour changed completely to yellow. The suspension was filtered and the filtration residue was washed with ethyl acetate (400 ml). The filtrate was diluted with ethyl acetate (800 ml) and the phases were separated. The organic phase was washed with water (2×250 ml) and the combined aqueous phases were re-extracted with ethyl acetate (2×200 ml). The combined organic phases were washed with saturated aqueous NaCl solution (200 ml), dried over Na$_2$SO$_4$, filtered, concentrated on the rotary evaporator and dried under fine vacuum. The crude product was purified by means of column chromatography (SiO$_2$, n-hexane/ethyl acetate 9:1). 38.4 g (95.9 mmol, 64% yield) of a yellow solid was obtained (mp: 47-50° C.)

$^1$H-NMR (CDCl$_3$, 400 MHz): δ=1.12 (t, 6H; J=7.9 Hz, —CH$_3$), 1.47 (q, 4H; J=7.9 Hz, Ge—CH$_2$—), 3.80 (s, 6H, O—CH$_3$), 6.87-6.91 (m, 4H, Ar—H$^{3,5}$), 7.71-7.75 (m, 4H, Ar—H$^{2,6}$).

$^{13}$C-NMR (CDCl$_3$, 100.6 MHz): δ=6.4 (—CH$_3$), 9.0 (Ge—CH$_2$—), 55.5 (O—CH$_3$), 114.1 (Ar—C$^{3,5}$), 130.5 (Ar—C$^{2,6}$), 135.0 (Ar—C$^1$), 163.8 (Ar—C$^4$), 227.4 (C=O).

Step 4: Bis-(4-hydroxybenzoyl)-diethylgermanium

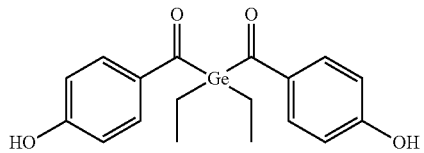

Bis-(4-methoxybenzoyl)diethylgermanium (8.0 g, 20.0 mmol) was dissolved in anhydrous toluene (200 ml) under protective gas and had Celatom (10 g) and aluminium chloride (9.6 g, 72.0 mmol) added to it. The reaction mixture was heated for 2 h under reflux. After cooling, water (10 ml) was added and the suspension was stirred for 10 min at room temperature. The solvent was removed on the rotary evaporator. The residue had ethyl acetate (300 ml) added to it. The suspension was stirred for 16 h at room temperature and filtered over a thin layer of silica gel. The filtrate was concentrated on the rotary evaporator. The oily brown residue had chloroform (200 ml) added to it. The suspension was stirred for 16 h at room temperature and filtered. The filtration residue was washed with chloroform (80 ml) and dried in the vacuum drying oven (50° C., 125 mbar). 4.23 g (11.3 mmol, 57% yield) of a light yellow solid was obtained (mp: 167-168° C.)

$^1$H-NMR (DMSO-d$_6$, 400 MHz): δ=1.04 (t, 6H; J=7.9 Hz, —CH$_3$), 1.38 (q, 4H; J=7.9 Hz, Ge—CH$_2$—), 6.88 (d, 4H; J=8.5 Hz, Ar—H$^{3,5}$), 7.58 (d, 4H; J=8.5 Hz, Ar—H$^{2,6}$), 10.53 (s, 2H, OH).

$^{13}$C-NMR (DMSO-d$_6$, 100.6 MHz): δ=6.1 (—CH$_3$), 8.9 (Ge—CH$_2$—), 115.7 (Ar—C$^{3,5}$), 130.3 (Ar—C$^{2,6}$), 133.3 (Ar—C$^1$), 162.7 (Ar—C$^4$), 225.5 (C=O).

Step 5:
Bis-(4-methacryloyloxybenzoyl)-diethylgermanium

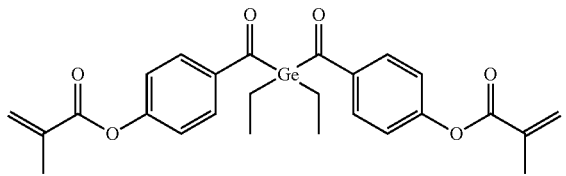

A solution of methacrylic anhydride (5.89 g, 38.2 mmol) and BHT (10 mg) in dichloromethane (50 ml) was added dropwise to a solution of bis-(4-hydroxybenzoyl)-diethylgermanium (6.78 g, 18.2 mmol), triethylamine (3.86 g, 38.2 mmol) and N,N-dimethylaminopyridine (240 mg, 2.0 mmol) in dichloromethane (100 ml) at −5° C. After addition was complete, the solution was stirred for 1 h at −5° C. and for 20 h at room temperature. The reaction solution was washed with water (3×100 ml). The combined aqueous phases were re-extracted with dichloromethane (2×50 ml). The combined organic phases were dried over Na$_2$SO$_4$, filtered, concentrated on the rotary evaporator and dried under fine vacuum. The crude product was purified by means of column chromatography (SiO$_2$, n-hexane/ethyl acetate 4:1). 4.40 g (8.6 mmol, 47% yield) of a yellow solid was obtained.

$^1$H-NMR (CDCl$_3$, 400 MHz): δ=1.13 (t, 6H; J=7.9 Hz, —CH$_3$), 1.51 (q, 4H; J=7.9 Hz, Ge—CH$_2$—), 2.04 (s, 6H, CH$_3$), 5.79-5.77 (m, 2H, C=CH), 6.34 (s, 2H, C=CH), 7.23-7.20 (m, 4H, Ar—H$^{3,5}$), 7.80-7.77 (m, 4H, Ar—H$^{2,6}$).

$^{13}$C-NMR (CDCl$_3$, 100.6 MHz): δ=6.5 (Ge—CH$_2$—), 9.0 (Ge—CH$_2$—$\underline{C}$H$_3$), 18.3 (CH$_3$), 122.3 (Ar C$^{3,5}$), 128.0 (C=$\underline{C}$H$_2$), 129.6 (Ar—C$^{2,6}$), 135.4 (C=C), 138.6 (Ar—C$^1$), 155.0 (Ar—C$^4$), 165.1 (C=O), 228.3 (Ge—C=O).

The invention claimed is:

1. Dental restorative material which comprises a thermolabile polymerizable compound of Formula II:

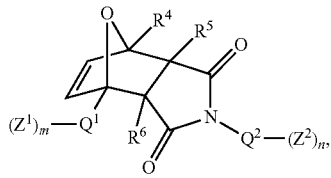

Formula II in which in each case independently of each other
one of $Z^1$ and $Z^2$ in each case independently represents a polymerizable group selected from CH$_2$=CR$^1$—CO—O— and CH$_2$=CR$^1$—CO—NR$^2$— and the other of $Z^1$ and $Z^2$ in each case independently represents an adhesive group selected from —Si(OR)3, —COOH, —O—PO(OH)2, —PO(OH)2, SO2OH and —SH, $Q^1$ in each case independently is missing or represents a C$_1$-C$_{10}$ radical, $Q^2$ in each case independently is missing or represents a C$_1$-C$_{10}$ radical, R in each case independently is CH$_3$ or C$_2$H$_5$,
$R^1$ in each case independently is H or CH$_3$,
$R^2$ in each case independently is H, CH$_3$ or C$_2$H$_5$,
$R^3$ in each case independently is H, CH$_3$ or C$_2$H$_5$,
$R^4$ is H, CH$_3$ or C$_2$H$_5$,
$R^5$ is H,
$R^6$ is H and/or
m and n in each case independently are 1 or 2.

2. Dental restorative material according to claim 1, which comprises one or more additional radically polymerizable monomers.

3. Dental restorative material according to claim 2, which comprises methyl, ethyl, hydroxyethyl, butyl, benzyl, tetrahydrofurfuryl or isobornyl (meth)acrylate, bisphenol-A-di(meth)acrylate, bis-GMA, UDMA, di-, tri- or tetraethylene glycol di(meth)acrylate, trimethylolpropane tri(meth)acrylate, pentaerythritol tetra-(meth)acrylate, glycerol di(meth)acrylate, 1,4-butanediol di-(meth)acrylate, 1,10-decanediol di(meth)acrylate, 1,12-dodecane-diol di(meth)acrylate, and/or one or more N-mono- or disubstituted acrylamides, N-ethyl-acrylamide, N,N-dimethacrylamide, N-(2-hydroxyethyl)acrylamide, N-methyl-N-(2-hydroxyethyl) acrylamide, one or more N-mono-substituted methacrylamides, N-ethylmethacrylamide, N-(2-hydroxyethyl)methacrylamide, N-vinylpyrrolidone, one or more cross-linking allyl ethers, and/or one or more cross-linking pyrrolidones, 1,6-bis(3-vinyl-2-pyrrolidonyl)-hexane, one or more cross-linking bisacryl-amides, methylene or ethylene bisacrylamide, one or more cross-linking bis(meth)acrylamides, N,N'-diethyl-1,3-bis(acrylamido)-propane, 1,3-bis(methacrylamido)-propane, 1,4-bis(acrylamido)-butane, 1,4-bis(acryloyl)-piperazine, and/or one or more thermolabile cross-linking monomers
or a mixture thereof.

4. Dental restorative material according to claim 1, which comprises one or more thermolabile cross-linking monomers.

5. Dental restorative material according to claim 1, which comprises one or more radically polymerizable, acid-group-containing monomers.

6. Dental restorative material according to claim 5, which comprises maleic acid, acrylic acid, methacrylic acid, 2-(hydroxymethyl)-acrylic acid, 4-(meth)acryloyloxyethyltrimellitic anhydride, 10-methacryloyloxydecylmalonic acid, N-(2-hydroxy-3-methacryl-oyloxypropyl)-N-phenylglycine, 4-vinylbenzoic acid, and/or vinylphosphonic acid, 4-vinylphenylphosphonic acid, 4-vinyl-benzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester
and/or
2-methacryloyloxypropyl mono- or dihydrogen phosphate, 2meth-acryloyloxyethylphenyl hydrogen phosphate, dipentaerythritol-pentamethacryloyloxyphosphate, 10-methacryloyloxydecyl dihydrogen phosphate, phosphoric acid mono-(1-acryloyl-piperidin-4-yl)-ester, 6-(methacrylamido)hexyl dihydrogen phosphate, 1,3-bis-(N-acryloyl-N-propyl-amino)-propan-2-yl-dihydrogen phosphate,
and/or
vinylsulphonic acid, 4-vinylphenylsulphonic acid, 3-(methacryl-amido)propylsulphonic acid,
or a mixture thereof.

7. Dental restorative material according to claim 1, which comprises an initiator for radical polymerization.

8. Dental restorative material according to claim 1, which comprises a thermally gas-releasing additive.

9. Dental restorative material according to claim 1, which comprises an additive which can convert radiated electromagnetic radiation into heat.

10. Dental restorative material according to claim 1, which comprises
a) 0.1 to 50 wt.-% compound of Formula II,
b) 0.01 to 10 wt.-% initiator,
c) 0 to 80 wt.-% comonomer,
d) 0 to 30 wt.-% adhesive monomer,
e) up to 80 wt.-% filler,
f) 0 to 70 wt.-% solvent.

11. Dental restorative material according to claim 1, which comprises
a) 1 to 40 wt.-% compound of Formula II,
b) 0.1 to 3.0 wt.-% initiator,
c) 1 to 60 wt.-% comonomer,
d) 0.5 to 15 wt.-% adhesive monomer,
e) up to 80 wt.-% filler,
f) 0 to 70 wt.-% solvent.

12. Dental restorative material according to claim 1, which comprises
a) 2 to 30 wt.-% compound of Formula II,
b) 0.2 to 2 wt.-% initiator,
c) 5 to 50 wt.-% comonomer,
d) 1 to 5 wt.-% adhesive monomer,
e) up to 80 wt.-% filler,
f) 0 to 70 wt.-% solvent.

13. Dental restorative material according to claim 1, which comprises
a) 5 to 30 wt.-% compound of Formula II,
b) 0.01 to 10 wt.-% initiator,
c) 0 to 80 wt.-% comonomer,
d) 0 to 30 wt.-% adhesive monomer,
e) up to 80 wt.-% filler,
f) 0 to 70 wt.-% solvent.

14. Dental restorative material according to claim 1, in which in each case independently of each other
$Q^1$ in each case independently is missing or represents a $C_1$-$C_8$ radical, and/or $Q^2$ in each case independently is missing or represents $C_1$-$C_8$ radical.

15. Dental restorative material according to claim 1, in which in each case independently of each other
$Q^1$ in each case independently is missing or represents a $C_2$-$C_6$ radical, and/or
$Q^2$ in each case independently is missing or represents a $C_2$-$C_6$ radical.

16. Dental restorative material according to claim 1, in which in each case independently of each other
$Q^1$ in each case independently is missing or represents $C_1$-$C_2$ radical, which can be interrupted by —O—, —CO—O—, —O—CO—, —CO—NR3-, —NR3-CO—, —O—CO—NR3-, —NR3-CO—O— or —NR3-CO—NR3-, and/or
$Q^2$ in each case independently is missing or represents a $C_2$-$C_3$ radical, which can be interrupted by —O—, —CO—O—, —O—CO—, —CO—NR$^3$—, —NR$^3$—CO—, —O—CO—NR$^3$—, —NR$^3$—CO—O— or —NR$^3$—CO—NR$^3$—.

* * * * *